(12) United States Patent
Sessions et al.

(10) Patent No.: US 12,207,801 B2
(45) Date of Patent: Jan. 28, 2025

(54) SYSTEMS, DEVICES, AND METHODS FOR SAMPLE COLLECTION

(71) Applicant: Ancestry.com DNA, LLC, Lehi, UT (US)

(72) Inventors: Travis Sessions, Cedar Hills, UT (US); Dan H. O'Neill, Salt Lake City, UT (US); Jacob Wakley, West Jordan, UT (US); William R. Barron, Riverton, UT (US); Ryan Patterson, Farmington, UT (US); Aaron Devore, Lehi, UT (US); Collin Sorensen, Orem, UT (US); Grant Daniels, Eagle Mountain, UT (US)

(73) Assignee: Ancestry.com DNA, LLC, Lehi, UT (US)

( * ) Notice: Subject to any disclaimer, the term of this patent is extended or adjusted under 35 U.S.C. 154(b) by 790 days.

(21) Appl. No.: 16/814,891

(22) Filed: Mar. 10, 2020

(65) Prior Publication Data

US 2020/0261066 A1     Aug. 20, 2020

Related U.S. Application Data

(63) Continuation of application No. 16/481,050, filed as application No. PCT/US2018/054136 on Oct. 3, 2018, now Pat. No. 10,973,497.

(Continued)

(51) Int. Cl.
*A61B 10/00* (2006.01)
*A61B 5/15* (2006.01)
*A61B 10/02* (2006.01)

(52) U.S. Cl.
CPC .... *A61B 10/0051* (2013.01); *A61B 5/150755* (2013.01); *A61B 10/0283* (2013.01)

(58) Field of Classification Search
None
See application file for complete search history.

(56) References Cited

U.S. PATENT DOCUMENTS 2,793,776 A     5/1957   Ipari
3,477,431 A  *  11/1969  Walecka ........... B05C 17/00593
                                                       206/221

(Continued)

FOREIGN PATENT DOCUMENTS

CN         205300987 U    6/2016
WO         WO-98/03265    1/1998

(Continued)

OTHER PUBLICATIONS

European Patent Office, Extended European Search Report and Opinion, EP Patent Application No. 18768389.1, Nov. 23, 2020, eight pages.

(Continued)

*Primary Examiner* — Matthew Kremer
(74) *Attorney, Agent, or Firm* — Fenwick & West LLP

(57) ABSTRACT

Provided herein are systems, devices, and methods for sample collection. A sample collection device may comprise a vessel, a lid, and pre-loaded liquid solutions. The sample collection device may collect a liquid sample, such as a biological sample. The liquid solutions may comprise reagents for preserving and/or stabilizing biological samples, such as saliva, collected in the vessel. A chamber comprising the liquid solutions may be located in the vessel and/or the lid. In some instances, the liquid solution may be released from the chamber upon closure of the vessel with the lid. In some instances, the liquid solution may be released from the chamber upon actuation of an implement, such as a plunger. In some instances, the liquid solution may be released upon compression of an absorbent member. The (Continued)

sample collecting device may be delivered to a remote location for further processing and/or analysis.

10 Claims, 6 Drawing Sheets

Related U.S. Application Data

(60) Provisional application No. 62/569,082, filed on Oct. 6, 2017.

(56) References Cited

U.S. PATENT DOCUMENTS

| | | | |
|---|---|---|---|
| 3,831,742 A | 8/1974 | Gardella et al. | |
| 4,131,016 A | 12/1978 | Layton | |
| 4,184,483 A | 1/1980 | Greenspan | |
| 4,217,798 A | 8/1980 | McCarthy et al. | |
| 4,301,812 A | 11/1981 | Layton et al. | |
| 4,312,950 A | 1/1982 | Snyder et al. | |
| 4,409,988 A | 10/1983 | Greenspan | |
| 4,449,645 A | 5/1984 | Korwin et al. | |
| 4,935,342 A | 6/1990 | Seligson et al. | |
| 4,982,553 A | 1/1991 | Itoh | |
| 5,283,038 A | 2/1994 | Seymour | |
| 5,393,496 A | 2/1995 | Seymour | |
| 5,396,986 A | 3/1995 | Fountain et al. | |
| 5,714,341 A | 2/1998 | Thieme et al. | |
| 5,736,322 A | 4/1998 | Goldstein | |
| 5,736,355 A | 4/1998 | Dyke et al. | |
| 5,830,154 A | 11/1998 | Goldstein et al. | |
| 5,830,410 A | 11/1998 | Thieme et al. | |
| 5,927,549 A | 7/1999 | Wood | |
| 5,933,498 A | 8/1999 | Schneck et al. | |
| 6,003,728 A | 12/1999 | Elliott | |
| 6,048,091 A | 4/2000 | McIntyre et al. | |
| 6,152,296 A | 11/2000 | Shih | |
| 6,196,979 B1* | 3/2001 | Virtanen | A61B 5/150755 |
| | | | 600/573 |
| 6,228,323 B1 | 5/2001 | Asgharian et al. | |
| 6,277,331 B1 | 8/2001 | Konrad | |
| 6,428,962 B1 | 8/2002 | Naegele | |
| 6,458,546 B1 | 10/2002 | Baker | |
| D470,240 S | 2/2003 | Niedbala et al. | |
| 6,543,612 B2* | 4/2003 | Lee | B65D 81/3222 |
| | | | 206/222 |
| 6,548,256 B2 | 4/2003 | Lienau et al. | |
| D474,280 S | 5/2003 | Niedbala et al. | |
| 6,627,152 B1 | 9/2003 | Wong | |
| 6,786,330 B2 | 9/2004 | Mollstam et al. | |
| D507,351 S | 7/2005 | Birnboim | |
| 6,939,672 B2 | 9/2005 | Lentrichia et al. | |
| 6,992,182 B1 | 1/2006 | Müller et al. | |
| 7,055,685 B1 | 6/2006 | Patterson et al. | |
| 7,178,683 B2 | 2/2007 | Birkmayer et al. | |
| 7,214,484 B2 | 5/2007 | Weber et al. | |
| 7,297,485 B2 | 11/2007 | Bornar et al. | |
| 7,303,876 B2 | 12/2007 | Greenfield et al. | |
| D574,507 S | 8/2008 | Muir et al. | |
| 7,482,116 B2 | 1/2009 | Birnboim | |
| 7,537,132 B2 | 5/2009 | Marple et al. | |
| 7,544,468 B2 | 6/2009 | Goldstein et al. | |
| 7,589,184 B2 | 9/2009 | Hogan et al. | |
| 7,645,424 B2 | 1/2010 | O'Donovan | |
| 7,748,550 B2 | 7/2010 | Cho | |
| 7,854,104 B2 | 12/2010 | Cronin | |
| 7,858,396 B2 | 12/2010 | Corstjens et al. | |
| D631,350 S | 1/2011 | Beach et al. | |
| D631,553 S | 1/2011 | Niedbala et al. | |
| 7,866,465 B2 | 1/2011 | Dverin | |
| D640,794 S | 6/2011 | Sunstrum et al. | |
| D640,795 S | 6/2011 | Jackson et al. | |
| 7,998,757 B2 | 8/2011 | Darrigrand et al. | |
| 8,038,668 B2 | 10/2011 | Scott et al. | |
| 8,062,908 B2 | 11/2011 | Mink et al. | |
| 8,158,357 B2 | 4/2012 | Birnboim et al. | |
| 8,221,381 B2 | 7/2012 | Muir et al. | |
| D673,265 S | 12/2012 | Nonnemacher et al. | |
| 8,425,864 B2 | 4/2013 | Haywood et al. | |
| 8,431,384 B2 | 4/2013 | Hogan et al. | |
| 8,470,536 B2 | 6/2013 | Birnboim et al. | |
| 8,673,239 B2 | 3/2014 | Niedbala et al. | |
| 8,728,414 B2 | 5/2014 | Beach et al. | |
| 9,040,675 B2 | 5/2015 | Bales et al. | |
| 9,072,499 B2 | 7/2015 | Birnboim et al. | |
| 9,079,181 B2 | 7/2015 | Curry et al. | |
| D743,044 S | 11/2015 | Jackson et al. | |
| D743,571 S | 11/2015 | Jackson et al. | |
| 9,207,164 B2 | 12/2015 | Muir et al. | |
| 9,410,147 B2 | 8/2016 | Gundling | |
| 9,416,356 B2 | 8/2016 | Gundling | |
| 9,523,115 B2 | 12/2016 | Birnboim | |
| 9,757,179 B2 | 9/2017 | Formica | |
| 10,000,795 B2 | 6/2018 | Birnboim et al. | |
| D850,647 S | 6/2019 | Jackson et al. | |
| 10,435,735 B2 | 10/2019 | Birnboim et al. | |
| 10,973,497 B2* | 4/2021 | Sessions | A61B 10/0096 |
| 2003/0089627 A1 | 5/2003 | Chelles et al. | |
| 2004/0132091 A1 | 7/2004 | Ramsey et al. | |
| 2006/0201948 A1 | 9/2006 | Ellson et al. | |
| 2006/0252054 A1 | 11/2006 | Lin et al. | |
| 2007/0170142 A1 | 7/2007 | Cho | |
| 2009/0024060 A1 | 1/2009 | Darrigrand et al. | |
| 2009/0216213 A1 | 8/2009 | Muir et al. | |
| 2010/0021351 A1* | 1/2010 | Hollander | B01L 3/502 |
| | | | 422/400 |
| 2010/0099149 A1 | 4/2010 | Birnboim et al. | |
| 2010/0258457 A1 | 10/2010 | Seelhofer | |
| 2011/0020195 A1 | 1/2011 | Luotola | |
| 2011/0028863 A1* | 2/2011 | Butlin | A61B 10/0051 |
| | | | 600/584 |
| 2011/0207621 A1 | 8/2011 | Montagu et al. | |
| 2011/0212002 A1 | 9/2011 | Curry et al. | |
| 2012/0024861 A1 | 2/2012 | Otsuka et al. | |
| 2012/0024862 A1 | 2/2012 | Otsuka et al. | |
| 2012/0046574 A1 | 2/2012 | Skakoon | |
| 2012/0061392 A1 | 3/2012 | Beach et al. | |
| 2012/0325721 A1 | 12/2012 | Plante et al. | |
| 2013/0037427 A1 | 2/2013 | Wu | |
| 2013/0092690 A1 | 4/2013 | Skakoon | |
| 2013/0164738 A1* | 6/2013 | Becker | A61B 10/0051 |
| | | | 435/306.1 |
| 2014/0005636 A1 | 1/2014 | Wang et al. | |
| 2014/0120531 A1 | 5/2014 | Biadillah et al. | |
| 2014/0316302 A1 | 10/2014 | Nonnemacher et al. | |
| 2015/0056716 A1 | 2/2015 | Oyler et al. | |
| 2017/0001191 A1 | 1/2017 | Biadillah et al. | |
| 2017/0016807 A1 | 1/2017 | Biadillah et al. | |
| 2017/0072393 A1 | 3/2017 | Jackson et al. | |
| 2017/0130219 A1 | 5/2017 | Birnboim et al. | |
| 2017/0166955 A1 | 6/2017 | Birnboim et al. | |
| 2017/0226469 A1 | 8/2017 | Birnboim et al. | |
| 2018/0036733 A1 | 2/2018 | Williams | |
| 2019/0210778 A1 | 7/2019 | Muir et al. | |
| 2019/0358628 A1 | 11/2019 | Curry et al. | |

FOREIGN PATENT DOCUMENTS

| | | | |
|---|---|---|---|
| WO | WO-2007009170 A1 * | 1/2007 | A61B 10/0045 |
| WO | WO 2012/177656 A2 | 12/2012 | |
| WO | WO 2016/079611 A1 | 5/2016 | |
| WO | WO 2016/131859 A1 | 8/2016 | |

OTHER PUBLICATIONS

United States Office Action, U.S. Appl. No. 16/481,050, Nov. 2, 2020, 21 pages.

European Patent Office, Extended European Search Report and Opinion, EP Patent Application No. 18864358.9, Jun. 1, 2021, eight pages.

Meulenbelt, I. et al. "High-Yield Noninvasive Human Genomic DNA Isolation Method for Genetic Studies in Geographically

(56) References Cited

OTHER PUBLICATIONS

Dispersed Families and Populations," American Journal of Human Genetics, 1995, vol. 57, No. 1252-1254, 3 pages.
Intellectual Property Australia, Examination Report, Australian Patent Application No. 2018234638, Oct. 28, 2022, four pages.
United States Office Action, U.S. Appl. No. 16/563,800, Aug. 2, 2022, 23 pages.
United States Office Action, U.S. Appl. No. 18/139,265, May 20, 2024, 18 pages.
European Patent Office, Examination Report, European Patent Application No. 18864358.9, Aug. 27, 2024, seven pages.

* cited by examiner

SYSTEMS, DEVICES, AND METHODS FOR SAMPLE COLLECTION

CROSS REFERENCE TO RELATED APPLICATIONS

This application is a continuation of prior, co-pending U.S. application Ser. No. 16/481,050, filed on Oct. 3, 2018, which is a national stage entry of International Application No.: PCT/US2018/054136, filed on Oct. 3, 2018, which claims the benefit of priority to U.S. Application No. 62/569,082, filed on Oct. 6, 2017, which is incorporated by reference herein in its entirety for all purposes.

BACKGROUND

Bodily fluids, such as saliva, sweat, urine, and blood, can be collected from a subject and analyzed to determine information contained in such samples of bodily fluids. For example, a sample may contain information pertaining to the subject. The sample may contain information pertaining to the environment inhabited by the subject. In some instances, the samples may comprise deoxyribonucleic acid (DNA) molecules that can be further processed and/or analyzed to determine genetic information about the subject.

Saliva is a bodily fluid generally secreted by the major salivary glands, such as the parotid, submandibular, and sublingual glands. Saliva may be collected non-invasively, such as by expelling directly from the mouth or inserting a collector, such as a swab, in the mouth to collect.

SUMMARY

On-site collection of biological samples, while relatively safe and guaranteeing a certain standard, can be inconvenient for several reasons. For example, a subject may have to travel a long distance to reach an on-site center (e.g., labs, hospitals, clinics, etc.), wasting valuable time, expenses, and other resources for a sample collection procedure that can be relatively simple especially for the types of samples (e.g., saliva) that can be collected non-invasively. For many subjects, no on-site center may be reasonably accessible. Furthermore, biological samples collected remotely and delivered to a lab for further processing or analysis are prone to contamination, spoiling, leakage, and/or loss which can present difficulties during such analysis, which can affect the cost of analysis, as well as both the speed and accuracy of the results. Thus recognized herein is a need for systems, devices, and methods for sample collection that can safely and securely deliver a biological sample between remote locations while preserving the integrity of the sample. There is a need for simple systems, devices, and methods that permit non-sophisticated users to collect a biological sample for delivery to a remote location.

Provided herein are systems, devices, and methods for sample collection. A sample collection device may comprise a vessel, a lid, and pre-loaded liquid solutions. The liquid solutions may comprise reagents that preserve and/or stabilize liquid samples collected in the vessel. The liquid solution may comprise other reagents. The liquid samples can comprise biological samples. A biological sample can be, for example, saliva. The biological sample can be sputum or spit. A chamber comprising the liquid solution (e.g., reagent) may be located in the vessel and/or the lid. In some instances, the reagent may be released from the chamber upon closure of the vessel with the lid. In some instances, the reagent may be released from the chamber upon actuation of an implement (e.g., plunger). The implement may be movable. In some instances, the reagent may be released upon compression of an absorbent member. The sample collection device may, such as through one or more of the abovementioned mechanisms, bring in contact or into fluid communication the liquid solution and the liquid sample. The sample collecting device, once securely closed, may be delivered to a remote location for further processing and/or analysis of the preserved and/or stabilized (or otherwise processed) sample.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure.

Accordingly, the drawings and description are to be regarded as illustrative in nature, and not as restrictive.

In one embodiment, a device for storing a liquid sample, comprises: a cap comprising one or more inner walls and a first engagement unit; and a vessel comprising a first set of one or more walls defining a cavity comprising an open end and a closed end, and a second engagement unit adjacent to said open end, wherein said second engagement unit is capable of engaging with said first engagement unit, and wherein said cavity comprises: an implement that comprises a second set of one or more walls at least partially defining a reservoir for storing said liquid sample, wherein said second set of one or more walls comprises at least one opening through which said reservoir is in fluid communication with said cavity; and a chamber at least partially defined by said first set of one or more walls, said closed end of said cavity, and said second set of one or more walls, wherein said chamber comprises a liquid solution, wherein said implement is movable along an axis of said cavity between (i) a first position and (ii) a second position, wherein movement of said implement from said first position to said second position subjects said liquid solution to flow from said chamber to said reservoir; and wherein upon said first engagement unit engaging with said second engagement unit, said cap closes said open end and subjects said implement to movement along said axis from said first position to said second position, thereby subjecting said liquid solution to flow from said chamber to said reservoir.

In one embodiment of the device, portions of said first set of one or more walls that are at or adjacent to said closed end comprise one or more serrations or protrusions.

In one embodiment of the device, at said second position, said second set of one or more walls interfaces with said one or more serrations or protrusions to disrupt a barrier between said first set of one or more walls and said second set of one or more walls.

In one embodiment of the device, at said first position, said second set of one or more walls interfacing with said first set of one or walls forms a barrier between said chamber and said reservoir through a seal.

In one embodiment of the device, at said first position, said second set of one or more walls interfaces with said one or more serrations or protrusions to seal said chamber from said reservoir.

In one embodiment of the device, said second set of one or more walls interfacing with said one or more serrations or protrusions seals said chamber through an interference fit.

In one embodiment of the device, said first engagement unit and said second engagement unit are a pair of complementary threads.

In one embodiment of the device, said implement is configured to lock at said second position.

In one embodiment of the device, said chamber has a first volume at said first position and a second volume at said second position, and wherein said first volume is greater than said second volume.

In one embodiment of the device, said axis is a vertical axis of said vessel.

In one embodiment of the device, at said first position, said chamber comprises said liquid solution in an amount that substantially fills said chamber.

In one embodiment of the device, said liquid sample is a biological sample.

In one embodiment of the device, said liquid solution is a reagent for stabilizing said biological sample.

In one embodiment of the device, the device further comprises a funnel comprising a first end, a second end, and a third engagement unit adjacent to said first end, wherein said third engagement unit is capable of removeably engaging with said second set of one or more walls, and upon engagement of said third engagement unit, said second end is brought into fluid communication with said reservoir.

In one embodiment of the device, said third engagement unit is configured to pinch together a given wall of said first set of one or more walls and a given wall of said second set of one or more walls.

In one embodiment of the device, upon engagement of said third engagement unit, said vessel and said implement are fixed relative to the other.

In one embodiment of the device, said third engagement unit comprises a clip configured to surround said given wall of said first set of one or more walls and said given wall of said second set of one or more walls.

In one embodiment of the device, upon engagement of said third engagement unit, said funnel seals said at least one opening in said implement, thereby fluidically isolating said chamber and said reservoir.

In one embodiment of the device, the device further comprises a container for shipping said device, wherein said container comprises a cavity that is dimensioned to receive and retain said device during shipping.

In one embodiment, a device for storing a liquid sample comprises: a cap comprising (i) a shell comprising a first engagement unit, (ii) a plate comprising at least one aperture, and (iii) a chamber at least partially defined by said plate, wherein said chamber comprises an absorbent matrix comprising a liquid solution, wherein said liquid solution is releasable from said absorbent matrix upon compression of said absorbent matrix; and a vessel comprising (i) one or more walls at least partially defining a reservoir for storing said liquid sample, and (ii) a compression unit that is configured to interface with said plate, wherein said vessel comprises a second engagement unit configured to engage with said first engagement unit, wherein upon said first engagement unit engaging with said second engagement unit, said cap closes said vessel and said compression unit interfaces with said plate to subject said absorbent matrix to compression, thereby releasing said liquid solution from said absorbent matrix through said at least one aperture to said reservoir.

In one embodiment of the device, said compression unit is part of said one or more walls.

In one embodiment of the device, said chamber is at least partially defined by said shell.

In one embodiment of the device, said first engagement unit and said second engagement unit are a pair of complementary threads.

In one embodiment of the device, said absorbent matrix is saturated with said liquid solution.

In one embodiment of the device, said absorbent matrix is not saturated with said liquid solution.

In one embodiment of the device, said plate is moveable into said chamber.

In one embodiment of the device, said plate is moveable with a limited degree of freedom.

In one embodiment of the device, said plate is moveable into said chamber by at most 5 cm.

In one embodiment of the device, said plate is moveable into said chamber in a substantially vertical direction.

In one embodiment of the device, said liquid sample is a biological sample.

In one embodiment of the device, said liquid solution is a reagent for stabilizing said biological sample.

In one embodiment of the device, the device further comprises a container for shipping said device, wherein said container comprises a cavity that is dimensioned to receive and retain said device during shipping.

In one embodiment, a method for collecting and storing a liquid sample, comprises using an embodiment of any of the devices described above to collect said liquid sample from a subject.

In one embodiment, a method for processing a liquid sample, comprises steps of:
(a) receiving a device as in any of the above embodiments, which device comprises said liquid sample collected from a subject; and (b) processing said liquid sample from said device.

In one embodiment of the method, said processing comprises subjecting said liquid sample to nucleic acid amplification.

In one embodiment of the method, said nucleic acid amplification comprises reverse transcription amplification and/or polymerase chain reaction.

In one embodiment of the method, said liquid sample comprises deoxyribonucleic acid (DNA), ribonucleic acid (RNA), and/or protein from said subject.

In one embodiment of the method, said processing comprises subjecting a nucleic acid and/or protein sample derived from said liquid sample to sequencing to determine a sequence of said nucleic acid and/or protein sample.

In one embodiment, a kit for collecting and storing a liquid sample, comprising: an embodiment of any of the devices described above; and instructions for directing a user to collect said liquid sample from a subject and store said liquid sample in said device. Said instructions may be provided on a physical medium accompanying said device or in an electronic medium, or both.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "FIG." herein) of which:

DETAILED DESCRIPTION

Figures 1A, 1B:
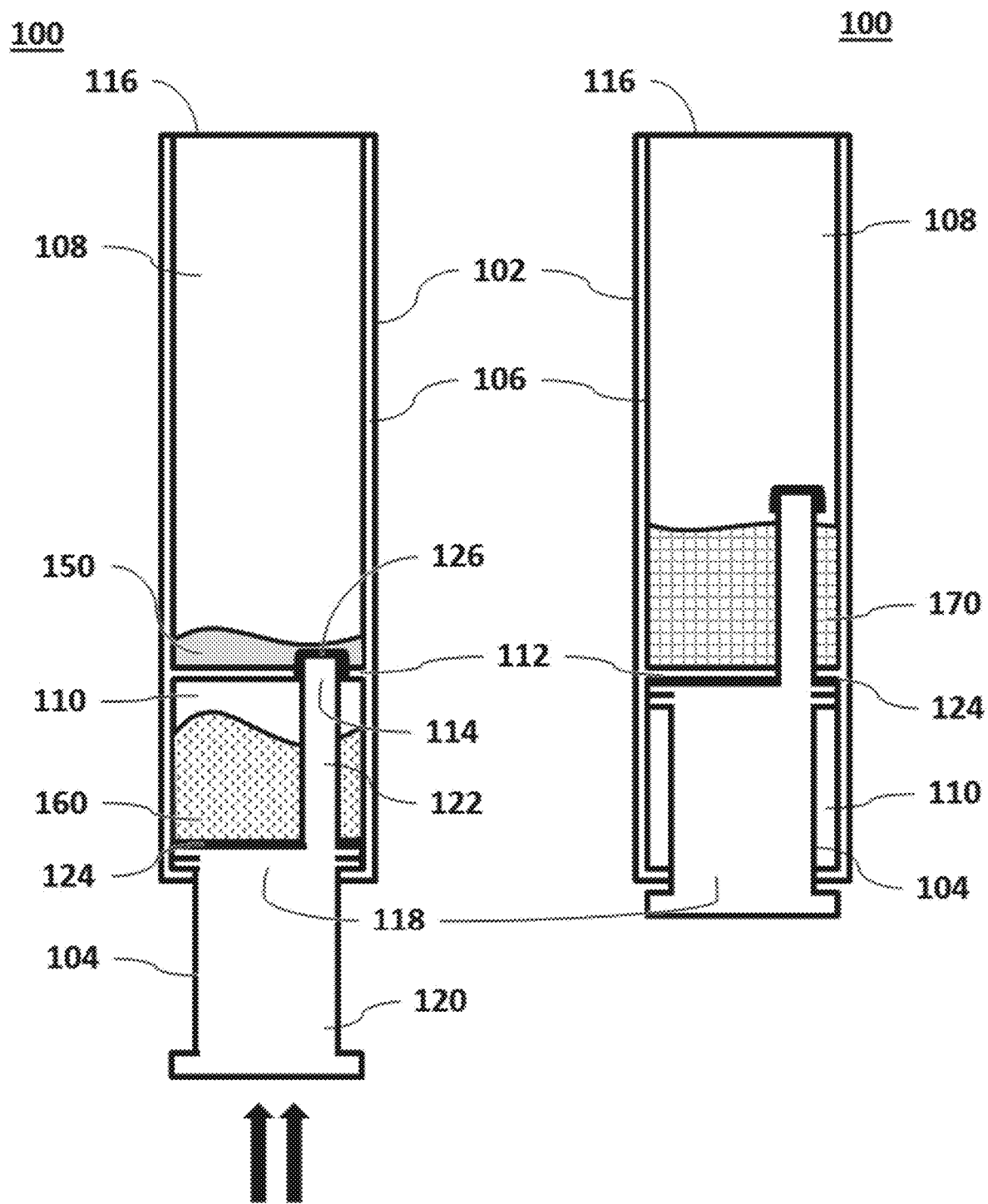
FIG. 1A shows a cross-sectional view of a sample collection device in an unengaged position, according to an embodiment.
FIG. 1B shows a cross-sectional view of the sample collection device of FIG. 1A in an engaged position, according to an embodiment.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The term "sample," as used herein, generally refers to a specimen for processing and/or analysis. A sample may be a liquid sample. A sample may be a fluid (e.g., gas, liquid) sample.

A sample may be a biological sample. The sample may be a bodily fluid. In an example, the bodily fluid is saliva, sputum, blood, perspiratory fluid (e.g., sweat), pus, tear, mucosal excretion, vomit, urine, stool, semen, vaginal fluids, or other type of bodily fluid. The sample can be a non-fluid sample. The sample can be a cell-free sample, such as a cell-free nucleic acid sample. The sample can include cell-free deoxyribonucleic acid (DNA), cell-free ribonucleic acid (RNA), and/or cell-free protein. The sample can include one or more cells (e.g., circulating tumor cells).

The sample can be a solid or tissue sample. The sample can be a skin sample. The sample can be a cheek swab or a swab of a different bodily part. The sample can be a homogenous sample or a heterogeneous sample. The sample can be a tumor sample, for instance. The sample can include one or more types of different biological samples (e.g., saliva and skin tissue). The sample may be derived from another sample. The sample can be a plasma or serum sample.

Alternatively or in addition to, the sample can be a non-biological sample (e.g., soil sample). Any description herein of any specific type of sample, such as sputum or saliva, may apply to any other type of sample.

The term "engagement unit," as used herein, generally refers to one or more features that are configured to engage with one or more other features. Examples of engagement units include, without limitation, one or more threads, interference fitting, hooks and loops, latches, screws, staples, clips, clamps, prongs, rings, brads, rubber bands, rivets, grommets, pins, ties, snaps, VELCRO, adhesives, tapes, vacuum, seals, or a combination thereof.

Systems, Devices, and Methods for Sample Collection

A sample may be collected from a subject and preserved and/or stabilized until such time of further processing and/or analysis, such as by contacting, or otherwise being exposed to, one or more reagents. For example, the collected sample, or one or more components thereof, may be preserved in their original state until such time of further processing and/or analysis. The collected sample, or one or more components thereof, may be preserved and/or stabilized to prevent bacterial or fungal growth. The collected sample may be preserved for at least 1 hours, 2 hours, 3 hours, 4 hours, 5 hours, 6 hours, 12 hours, 1 day, 2 days, 3 days, 4 days, 5 days, 6 days, 7 days, 1 week, 2 weeks, 3 weeks, 4 weeks, 1 month, 2 months, 3 months, 4 months, 5 months, 6 months, 1 year, 2 years, 3 years, or for longer durations. The collected sample may be preserved and stored at room temperature or lower for prolonged periods of time, such as during transit and/or storage. The collected sample may be preserved and stored at ambient temperatures or lower for prolonged periods of time, such as to ensure preservation during transit (e.g., shipping warehouses, etc.) and/or storage. Alternatively or in addition, the collected sample may be preserved at temperatures of up to about 60° Celsius (° C.).

As used herein, a reagent may refer to any kind of substance acting on the collected sample to achieve a desired effect. The reagent may be in any suitable form, such as a fluid (e.g., liquid, gas, solution, etc.) or a non-fluid (e.g., solid powder, etc.). In some instances, the reagent can be configured to preserve deoxyribonucleic acid (DNA), ribonucleic acid (RNA), proteins, or other components of proteins in the sample. In some instances, the reagent can be configured to prevent one or more cells from having their antigens degraded and/or prevent alterations in the cellular epigenome of one or more cells. The reagent may permit extraction of one or more constituents (e.g., nucleic acid molecules) from a cell from the collected sample. The reagent may be configured to otherwise process the collected sample and/or one or more constituents thereof. A liquid solution may comprise one or more reagents configured to achieve one or more desired affects.

Beneficially, the systems, devices, and methods provided herein may facilitate convenient and simple at-home, on-site, or remote collection of samples. Non-sophisticated users, and even minors, may be capable of collecting samples without direct supervision. Users of a sample collection device may advantageously be shielded from direct exposure to chemical reagents, which may or may not be toxic, that are pre-loaded in the sample collection device at any point during the sample collection process. In some instances, users may be provided with easy-to-follow instructions. The instructions may instruct on how to use a device, collect a sample using the device, dispose (e.g., ship to a remote location) of the device after use, access results from analysis of the sample, or other instructions. The collected sample may be transported, such as via shipping (e.g., through the mail or a carrier), to a remote lab for further processing and/or analysis.

The stabilized and/or preserved sample can be further processed and analyzed at an outside facility (e.g., remote facility). For example, nucleic acids (e.g., DNA, etc.) from the sample can be isolated and extracted for amplification and/or sequencing applications.

Reference is now made to the figures. It will be appreciated that the figures and features therein are not necessarily drawn to scale.

FIG. 1A shows a cross-sectional view of a sample collection device 100 in an unengaged position. FIG. 1B shows a cross-sectional view of the sample collection device 100 in an engaged position. The sample collection device 100 can comprise a vessel 102 and a plunger 104 that is insertable in the vessel 102. The vessel 102 can comprise one or more walls 106 that define a reservoir 108 for receiving a biological sample 150 and a reagent chamber 110 to hold a preservation reagent 160. The one or more walls can be formed of a polymeric material (e.g., polypropylene, polystyrene, polycarbonate, etc.), metallic material (e.g., aluminum), and/or composite material. The reservoir 108 and the reagent chamber 110 can be separated by an integral web 112. In some instances, the integral web 112 can be a part of the one or more walls 106. Alternatively or in addition, the integral web 112 can be a separate structure fastened to the one or more walls 106. The integral web 112 can have an aperture 114 through which the reservoir 108 and the reagent chamber 110 are in fluid communication. The reservoir 108 can have an opening 116 to receive the biological sample 150 from a user. The user may be a subject from whom the sample is collected. For example, the user can spit into the reservoir 108 through the opening. The reagent chamber 110 can comprise an opening 118.

The plunger 104 can comprise a first end 120 and a second end 122. The first end 120 can be configured to seal the opening 118 of the reagent chamber 110 to prevent the reagent 160 from leaving the reagent chamber 110 through the opening 118. For example, the first end 120 can comprise a lower gasket 124 that spans an inner cross-section of the reagent chamber 110.

The lower gasket 124 can have an interference fit to the inner dimensions of the reagent chamber 110 and provide a fluid-tight seal to prevent the reagent 160 from reaching or passing through the opening 118. The seal can be a hermetic seal. Any description herein of a plunger may apply to any other implement, such as a rod, stage, plate, or other actuator.

The first end 120 can be configured to enter the reagent chamber 110 through the opening 118 when the plunger 104 is injected into the vessel 102. The lower gasket 124 may continue to seal the opening 118, such as via the interference fit, as the plunger 104 is injected into the vessel 102. That is, the reagent 160 can be contained in the reagent chamber 110 between the lower gasket 124 and the integral web 112.

The second end 122 can be configured to seal the aperture 114 in the integral web 112 to prevent the reagent 160 from entering the reservoir 108 through the aperture 114 and prevent the biological sample 150 from entering the reagent chamber 110 through the aperture 114. For example, the second end 122 can comprise an upper gasket 126 at its tip that spans a cross-section of the aperture 114. The upper gasket 126 can have an interference fit to the aperture 114 and provide a fluid-tight seal to fluidically isolate the reservoir 108 from the reagent chamber 110 when the upper gasket 126 is in place. The seal can be a hermetic seal.

The second end 122 can be configured to enter the reservoir 108 through the aperture 114 when the plunger 104 is injected into the vessel 102. The seal (e.g., interference fit) from the upper gasket 126 can be broken (or released) as the tip of the second end 122 having the upper gasket 126 passes the aperture 114. When the seal is broken, the reservoir 108 and the reagent chamber 110 can be in fluid communication with the other. That is, the biological sample 150 may enter the reagent chamber 110 and/or the reagent 160 may enter the reservoir 108 to form a mixture 170 of the biological sample 150 and the reagent 160. When the plunger 104 is fully injected into the vessel 102, the lower gasket 126 may reach the integral web 112 such that the mixture 170 is directed into the reservoir 108.

In some instances, the plunger 104 may not be removed from the vessel 102 by the user. For example, a cross-section of a pre-inserted part of the first end 120 of the plunger 120 may be larger than a cross-section of the opening 118 of the reagent chamber 110.

The opening 116 of the reservoir 108 can be closed by a cap or lid (not shown) that is fastened or coupled to the vessel 102, such as to the one or more walls 106 of the vessel 102, to cover the opening 116. Fastening or coupling can be achieved by engagement units, such as via fastening or coupling mechanisms. Example of engagement units include, but are not limited to, complementary threading, form-fitting pairs, interference fitting, hooks and loops, latches, screws, staples, clips, clamps, prongs, rings, brads, rubber bands, rivets, grommets, pins, ties, snaps, velcro, adhesives, tapes, vacuum, seals, or a combination thereof. Any description herein of any specific type of fasteners, engagement units, fastening mechanisms, coupling mechanisms, or engagement mechanisms, such as threads or threading, may apply to any other type of fasteners, engagement units, fastening mechanisms, coupling mechanisms, or engagement mechanisms. For example, a cap with threads fastened to a vessel with complementary threads by threading to close the vessel may be interchanged with a stopper fastened to the vessel via form-fitting seal to close the vessel. The cap may seal the vessel 102. The seal can be fluid-tight. The seal can be a hermetic seal.

In application, the device 100 is provided to the user in an unengaged position (as in FIG. 1A). The reagent 160 is pre-loaded in the reagent chamber 110 and the plunger 104 is disposed in the vessel 102 such that the upper gasket 126 is sealing the aperture 114 in the integral web 112 and the lower gasket 124 is sealing the opening 118 in the reagent chamber 110. The plunger 104 is insertable into the vessel 102. The user spits or otherwise deposits the biological sample 150 into the reservoir 108 through the opening 116.

The user can close the opening 116 of the reservoir 108 with a cap or lid (not shown). Thereafter, the biological sample 150 is sealed in the reservoir 108 and fluidically isolated from the reagent compartment 110, and the reagent 160 is sealed in the reagent compartment 110 and fluidically isolated from the reservoir 108. The user then applies a force to inject the plunger 104 into the vessel 102. In an example, this can be accomplished by using one or more hands to push or press the plunger 104 inwards. In another example, this can be accomplished by holding the vessel 102 and pushing the plunger 104 end of the vessel 102 against any surface (e.g., floor, wall, desk surface, etc.). Once injected, the seal of aperture 114 is broken (or released) and the reservoir 108 and the reagent chamber 110 are brought in fluid communication with each other. The biological sample 150 and the reagent 160 form a mixture 170 of the biological sample 150 and the reagent 160.

When the plunger 104 is fully injected (as in FIG. 1B), the lower gasket 124 reaches the integral web 112, and the mixture 170 is directed into the reservoir 108. In some instances, once injected, the plunger 104 can lock in the injected position such that the mixture 170 stays in the reservoir 108. In other instances, after injection, the plunger 104 can be uninjected, and the mixture 170 can freely travel between the reservoir 108 and the reagent chamber 110. The plunger 104 may not be removed from the vessel 102 by the user. For example, a cross-section of a pre-inserted part of the first end 120 of the plunger 120 may be larger than a cross-section of the opening 118 of the reagent chamber 110.

The user may transport the device 100, such as via shipping, to a remote location such as an outside lab for further processing and/or analysis. The device 100 may be shipped in a container with or without insulation. For example, the container can be an envelope, packaging, and/or a box. The device 100 may withstand routine forces received in shipping environments.

In some instances, the user may inject the plunger 104 before closing the opening 116 of the reservoir 108 with the cap or lid. In some instances, the user may inject the plunger 104 before depositing the biological sample 150 in the reservoir 108.

In some instances, the integral web 112 can have a plurality of apertures, and the plunger 104 can have corresponding structures and components (e.g., plurality of gaskets) to seal the plurality of apertures. In some instances, the reagent compartment 110 can have a plurality of openings, and the plunger 104 can have corresponding structures and components (e.g., plurality of gaskets) to seal the plurality of openings.

In some instances, in the unengaged position (as in FIG. 1A) the reagent chamber 110 may be fully pre-loaded with the reagent 160 to fill the reagent chamber 110. Alternatively, the reagent chamber 110 may be partially pre-loaded with the reagent 160.

In some instances, the one or more walls 106 of the vessel 102 may comprise one or more markings corresponding to fluid volume for reference to users (e.g., sample origin, lab technician, etc.) of the device 100. For example, one or more markings may correspond to a volume of the reagent 160 in the reagent compartment 110. One or more markings may correspond to a volume of the biological sample 150 in the reservoir 108. One or more marking may correspond to a volume of the mixture 170 in the reservoir 108. In some instances, at least a part of the one or more walls 106 of the vessel may be at least partially transparent and/or translucent, or clear, to permit visual recognition of the one or more markings.

While FIGS. 1A and 1B illustrate a device with the reservoir 108 and the reagent chamber 110 as vertically neighboring compartments, other configurations are available where the reservoir 108 and the reagent chamber 110 are fluidically communicating through the aperture 114. For example, the reservoir 108 and the reagent chamber 110 can be horizontally neighboring compartments, diagonally neighboring compartments, or placed relative to the other in any other orientation with an aperture 114 fluidically connecting the two compartments.

In some instances, the aperture 114 can define a fluid path, such as a straight and/or curved cross-sectional path and the plunger 104 can have a corresponding structure to seal the aperture 114 and/or enter the aperture 114. For example, the aperture 114 can have a curvature, and the second end 122 can have a corresponding curvature to travel through the aperture 114. In some instances, the reagent chamber 110 can define a straight or curved path for the plunger 104 to be injected in, and the plunger 104 can have a corresponding structure to seal the opening 118 and/or enter the reagent chamber 110. For example, the path can have a curvature, and the first end 120 can have a corresponding curvature to travel through the path.

In some instances, the user can deposit the biological sample 150 into the reservoir 108 on a carrier. For example, the carrier can be an absorbent member, such as a swab, cotton, pad, sponge, foam, or other material or device capable of carrying the biological sample 150 by absorbing. When the reagent 160 is directed to the reservoir 108 by actuation of the plunger 104, the absorbent member may absorb the reagent 160, thereby contacting the biological sample 150 therein with the reagent 160 to preserve and/or stabilize the biological sample 150. The carrier can be other materials or device capable of carrying the biological sample 150 in a location that is in fluid communication with the reservoir 108 such as to allow the reagent 160 to contact the biological sample 150 on the carrier.

In an example, the user uses the device 100 to collect the biological sample 150 (e.g., saliva or cheek swab) from a subject. The user can be the subject. Alternatively, the user can be one or more other individuals (e.g., supervisor, guardian, lab technician, worker, etc.) that collect the biological sample 150 from the subject. The biological sample 150 is deposited into the sample reservoir 108 through the opening 116. Next, the user actuates the plunger 104, such as by pushing the plunger 104 into the vessel 102. The reagent 160 is directed into the reservoir 108 and forms a mixture 170 with the biological sample 150. The user closes the opening 116 with a lid (not shown). The closed device 100 is then transported (e.g., via mail), such as to a remote lab for further processing and/or analysis. The biological sample 150 is preserved and/or stabilized during such transportation with aid of the reagent 160.

Any description herein of a biological sample (e.g., biological sample 150) with reference to the device 100 can apply to a liquid sample. Any description herein of a reagent (e.g., reagent 160) with reference to the device 100 can apply to a liquid solution. For example, the device 100 may be pre-loaded with a liquid solution and facilitate collection of a liquid sample.

Figures 2A, 2B:
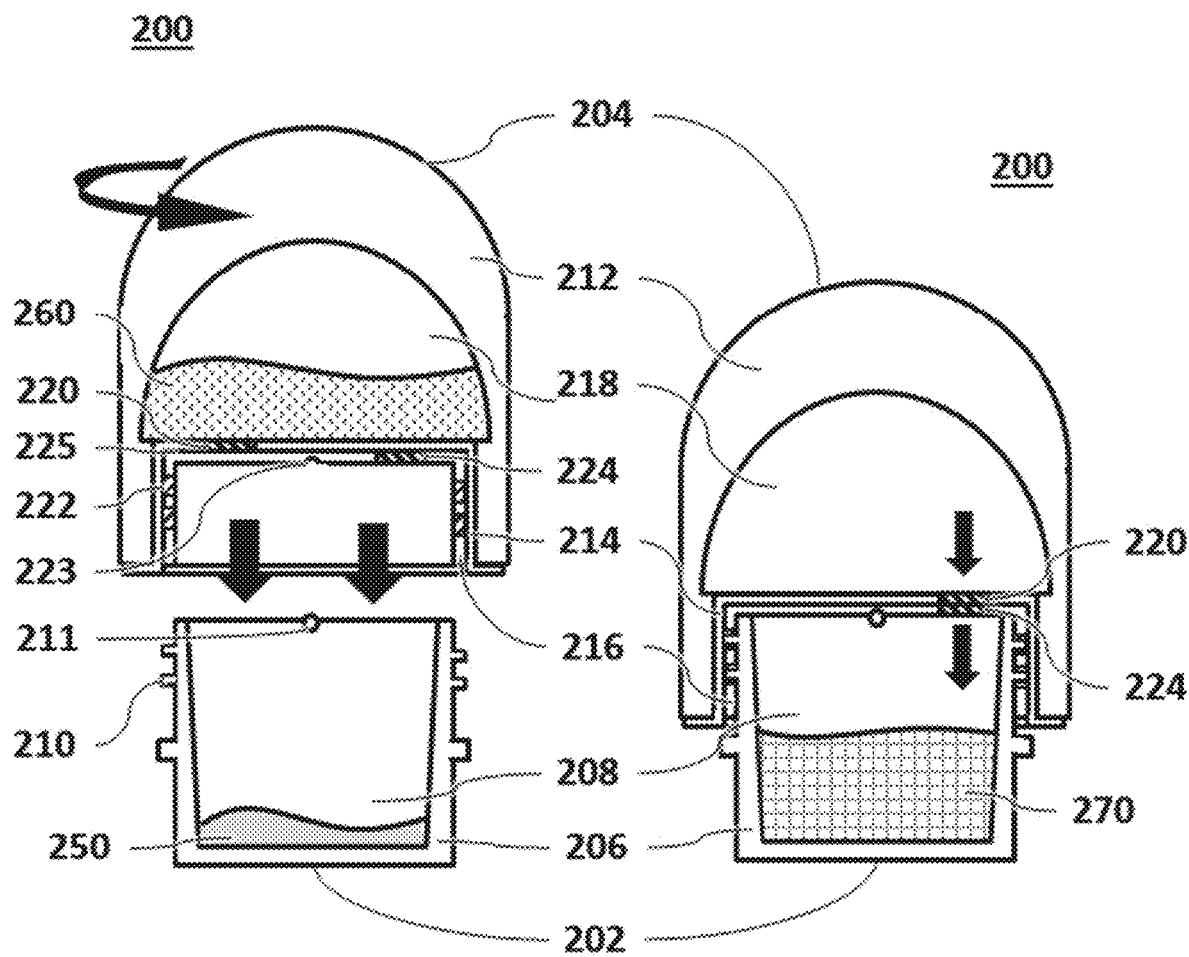
FIG. 2A shows a cross-sectional view of another sample collection device in an open position, according to an embodiment.
FIG. 2B shows a cross-sectional view of the sample collection device of FIG. 2A in a closed position, according to an embodiment.

FIG. 2A shows a cross-sectional view another sample collection device 200 in an open position. FIG. 2B shows a cross-sectional view of the sample collection device 200 in a closed position. The sample collection device 200 can comprise a vessel 202 and a lid 204.

The vessel 202 can comprise one or more walls 206 that define a reservoir 208 for receiving a biological sample 250 from a user. The user may be a subject from whom the sample is collected. The one or more walls 206 can comprise a first lid engagement unit 210, such as threads, to couple with the lid 204. The vessel 202 can comprise a second lid engagement unit 211, such as a rod or beam (wherein FIG. 2A shows a cross-section of a rod or beam which length is extending into the plane), to couple with the lid 204.

The lid 204 can comprise an outer shell 212, an inner wall 214, and a sleeve 216. The outer shell 212 can be fused or otherwise fastened to an inner wall 214. When fastened, the inner wall 214 can be fixed relative to the outer shell 212. The outer shell 212 and the inner wall 214 can enclose and define a reagent chamber 218. The reagent chamber 218 can comprise a preservation and/or stabilization reagent 260 for preserving and/or stabilizing the biological sample 250. The inner wall 214 can comprise an aperture 220 through which the reagent 260 may leave the reagent chamber 218.

The inner wall 214 can be mechanically assembled or otherwise fastened to a sleeve 216. A surface (e.g., bottom surface) of the inner wall 214 can interface a surface (e.g., top surface) of the sleeve 216. When fastened, the surface of the inner wall 214 may rotate relative to the surface of the sleeve 216 while interfacing the surface of the sleeve 216. In some instances, the inner wall 214 may rotate relative to the sleeve 216 only when sufficient torque is applied, such as to overcome frictional resistance. For example, this frictional resistance can be provided by a sealant 225, adhesive, or other material disposed between the inner wall 214 and the sleeve 216. The resistance can be provided by a mechanical element (e.g., stopper, blocking unit) in the mechanical assembly of the inner wall 214 and the sleeve 216. In some instances, the inner wall 214 may rotate relative to the sleeve 216 only when a mechanical trigger is engaged (e.g., removal of a blocking unit, etc.).

The sleeve 216 can comprise a first vessel engagement unit 222, such as threads complementary to the first vessel engagement unit 210. The sleeve 216 can comprise a second vessel engagement unit 223, such as a depression complementary to the second lid engagement unit 211. The sleeve 216 can comprise an aperture 224. In some instances, the sealant 225 can be disposed between the interfacing surface of the inner wall 214 and the interfacing surface of the sleeve 216 to provide a fluid-tight seal between the two surfaces such that fluid does not seep between the interfacing surfaces. The seal can be a hermetic seal. For example, the sealant 225 can be a silicone coating.

In an open position (as in FIG. 2A), the sleeve 216 can be mechanically assembled to the inner wall 214 such that the first aperture 220 in the inner wall 214 is blocked by a surface (e.g., top surface) of the sleeve 216 and the second aperture 224 in the sleeve 216 is blocked by a surface (e.g., bottom surface) of the inner wall 214. Because the first aperture 220 is blocked by the sleeve 216, the reagent 260 is fluidically confined to the reagent compartment 218 defined by the outer shell 212 and the inner wall 214.

To alternate to the closed position (as in FIG. 2B), the vessel 202 can be closed with the lid 204 by coupling the first vessel engagement unit 222 with the first lid engagement unit 210, such as via a threading motion. As the lid 204 descends to cover the vessel 202, the second vessel engagement unit 223 in the sleeve 216 can engage with the second lid engagement unit 211 in the vessel 202 to fix the sleeve 216 in position relative to the vessel 202. When the sleeve 216 is fixed relative to the vessel 202, a continued threading motion of the lid 204 can provide sufficient torque to rotate the inner wall 214 (and the fixed outer shell 212) relative to the sleeve 216. As the inner wall 214 rotates relative to the sleeve 216, the first aperture 220 in the inner wall 214 can at least partly align with the second aperture 224 in the sleeve 216 to bring the reagent chamber 218 in fluid communication with the reservoir 208. When the first aperture 220 and the second aperture 224 at least partly align, the reagent 260 in the reagent chamber 218 can flow into the reservoir 208 to form a mixture 270 with the biological sample 250. The biological sample 250 can thereby be preserved and/or stabilized in the mixture 270.

In application, the user is provided the device 200 in an open position (as in FIG. 2A). The reagent 260 is pre-loaded in the reagent chamber 218 in the lid 204 and fluidically isolated from the reservoir 208 or any other space external to the lid 204. The inner wall 214 and the sleeve 216 are mechanically assembled such that the sleeve 216 is blocking the aperture 220 of the inner wall 214. In some instances, the sealant 225 is disposed between the interfacing surfaces of the inner wall 214 and the sleeve 216 to provide a fluid tight seal in the interface of the inner wall 214 and the sleeve 216. The user spits or otherwise deposits the biological sample 250 into the reservoir 208 through an opening of the reservoir 208 in the vessel 202.

The user can close the vessel 202 with the lid 204. As the lid 204 is brought in proximity to the vessel 202, the first lid engagement unit 210 (e.g., threads) in the vessel 202 engages the first vessel engagement unit 222 (e.g., complementary threads) in the lid 204. The lid 204 descends with a threading motion until the second lid engagement unit 211 (e.g., rod, beam, etc.) in the vessel 202 engages the second vessel engagement unit 223 (e.g., depression) in the lid 204. The engagement of the second lid engagement unit 211 and the second vessel engagement unit 223 fixes the sleeve 216 relative to the vessel 202. As the user continues the threading motion on the lid 204, the user applies a sufficient torque to rotate the inner wall 214 (and the rest of the lid 204 assembly) relative to the sleeve 216. Upon rotation of the inner wall 214 relative to the sleeve 216, the aperture 220 in the inner wall 214 and the aperture 224 in the sleeve 216 at least partially align, thereby bringing into fluid communication the reagent chamber 218 and the reservoir 208. The reagent 260 flows into the reservoir 208 to form a mixture 270 of the reagent 260 and the biological sample 250. The biological sample 250 can thereby be preserved and/or stabilized in the mixture 270. In some instances, the reagent 260 may flow into the reservoir 208 via gravitational forces.

Thereafter, the lid 204 is fastened to the vessel 202 and the mixture 270 is confined in the reservoir 208 and optionally in the reagent compartment 218 which is in fluid communication with the reservoir 208. In some instances, the user may twist or rotate the lid 204 relative to the vessel 202 in some amount (e.g., 180°) in a direction opposite to the direction of closing to rotate the inner wall 214 relative to the sleeve 216 such that the aperture 224 in the sleeve 216 is blocked by the inner wall 214 and the mixture 270 is fluidically isolated in the reservoir 208.

The user may transport the device 200, such as via shipping, to a remote location such as an outside lab for further processing and/or analysis. The device 200 may be shipped in a container with or without insulation. For example, the container can be an envelope, packaging, and/or a box. The device 200 may withstand routine forces received in shipping environments.

In some instances, the user can deposit the biological sample 250 into the reservoir 208 on a carrier. For example, the carrier can be an absorbent member, such as a swab, cotton, pad, sponge, foam, or other material or device capable of carrying the biological sample 250 by absorbing.

When the reagent 260 flows in the reservoir 208, the absorbent member may absorb the reagent 260, thereby contacting the biological sample 250 therein with the reagent 260 to preserve and/or stabilize the biological sample 250. The carrier can be other materials or device capable of carrying the biological sample 250 in a location that is in fluid communication with the reservoir 208 such as to allow the reagent 260 to contact the biological sample 250 on the carrier.

In some instances, the inner wall 214 and the sleeve 216 may be mechanically assembled such that the inner wall 214 may rotate relative to the sleeve 216 with a limited degree of freedom. For example, the inner wall 214 may rotate relative to the sleeve 216 at most by 3 turns (1080°), 2.5 turns (900°), 2 turns (720°), 1.5 turns (540°), 1 turn (360°), 330°, 300°, 270°, 240°, 210°, 180°, 150°, 140°, 130°, 120°, 110°, 100°, 90°, 80°, 70°, 60°, 50°, 40°, 30°, 20°, 10°, 5°, or less. In some instances, the inner wall 214 and the sleeve 216 may be mechanically assembled such that the inner wall 214 may rotate relative to the sleeve 216 in either direction (e.g., clockwise, and counterclockwise). Alternatively, the inner wall 214 and the sleeve 216 may be mechanically assembled such that the inner wall 214 may rotate relative to the sleeve 216 in only one direction (e.g., clockwise, counterclockwise).

In some instances, the inner wall 214 can comprise a plurality of apertures, such as 2, 3, 4, 5, 6, 7, 8, 9, 20, or more apertures. The sleeve 224 can comprise an appropriate number of apertures to bring the reagent chamber 218 in fluid communication with the reservoir 208 through the plurality of apertures in the inner wall 214 when the device 200 is in a closed position.

In some instances, in the open position (as in FIG. 2A) the reagent chamber 218 may be fully pre-loaded with the reagent 260 to fill the reagent chamber 210. Alternatively, the reagent chamber 218 may be partially pre-loaded with the reagent 260.

In some instances, the one or more walls 206 of the vessel 202 may comprise one or more markings corresponding to fluid volume for reference to users (e.g., sample origin, lab technician, etc.) of the device 200. For example, one or more markings may correspond to a volume of the biological sample 250 in the reservoir 208. One or more marking may correspond to a volume of the mixture 270 in the reservoir 208. In some instances, at least a part of the one or more walls 206 of the vessel 202 may be at least partially transparent and/or translucent, or clear, to permit visual recognition of the one or more markings. In some instances, the outer shell 212 of the lid 204 may comprise one or more markings corresponding to fluid volume for reference to users (e.g., sample origin, lab technician, etc.) of the device 200. For example, one or more markings may correspond to a volume of the reagent 260 in the reagent compartment 210. In some instances, at least a part of the outer shell 212 of the lid 204 may be at least partially transparent and/or translucent, or clear, to permit visual recognition of the one or more markings.

In some instances, the lid 204 may be coupled to the vessel 202 via one or more other coupling or fastening mechanisms described elsewhere herein. As an example, the inner diameter of the sleeve 216 may form-fit the outer diameter of the vessel 202 and allow fastening of the two components without need for a threading motion or threading features, and the inner wall 214 may rotate relative to the sleeve 216 to open and/or close fluid communication between the reagent chamber 218 and the reservoir 208. As another example, the locations of the threads may be inverted such that the threads are on the inner walls of the vessel 202 and on the outer walls of the sleeve 216 and the sleeve 216 threads inside the vessel 202. In such a case, the inner wall 214 and outer shell 212 may be outside the vessel 202 when in a closed position.

In an example, the user uses the device 200 to collect the biological sample 250 (e.g., saliva or cheek swab) from a subject. The user can be the subject. Alternatively, the user can be one or more other individuals (e.g., supervisor, guardian, lab technician, worker, etc.) that collect the biological sample 250 from the subject. The biological sample 250 is deposited into the reservoir 208. Next, the user closes the vessel 202 with the lid 204, such as by engaging (e.g., threading) the lid 204 with the vessel 202. Upon engagement, the first aperture 220 and the second aperture 224 at least partially align, bringing the reagent chamber 218 in fluid communication with the reservoir 208. The reagent 260 is directed into the reservoir 208 through the first and second apertures 220, 224 and forms a mixture 270 with the biological sample 250. The closed device 200 is then transported (e.g., via mail), such as to a remote lab for further processing and/or analysis. The biological sample 250 is preserved and/or stabilized during such transportation with aid of the reagent 260.

Any description herein of a biological sample (e.g., biological sample 250) with reference to the device 200 can apply to a liquid sample. Any description herein of a reagent (e.g., reagent 260) with reference to the device 200 can apply to a liquid solution. For example, the device 200 may be pre-loaded with a liquid solution and facilitate collection of a liquid sample.

Figures 3A, 3B:
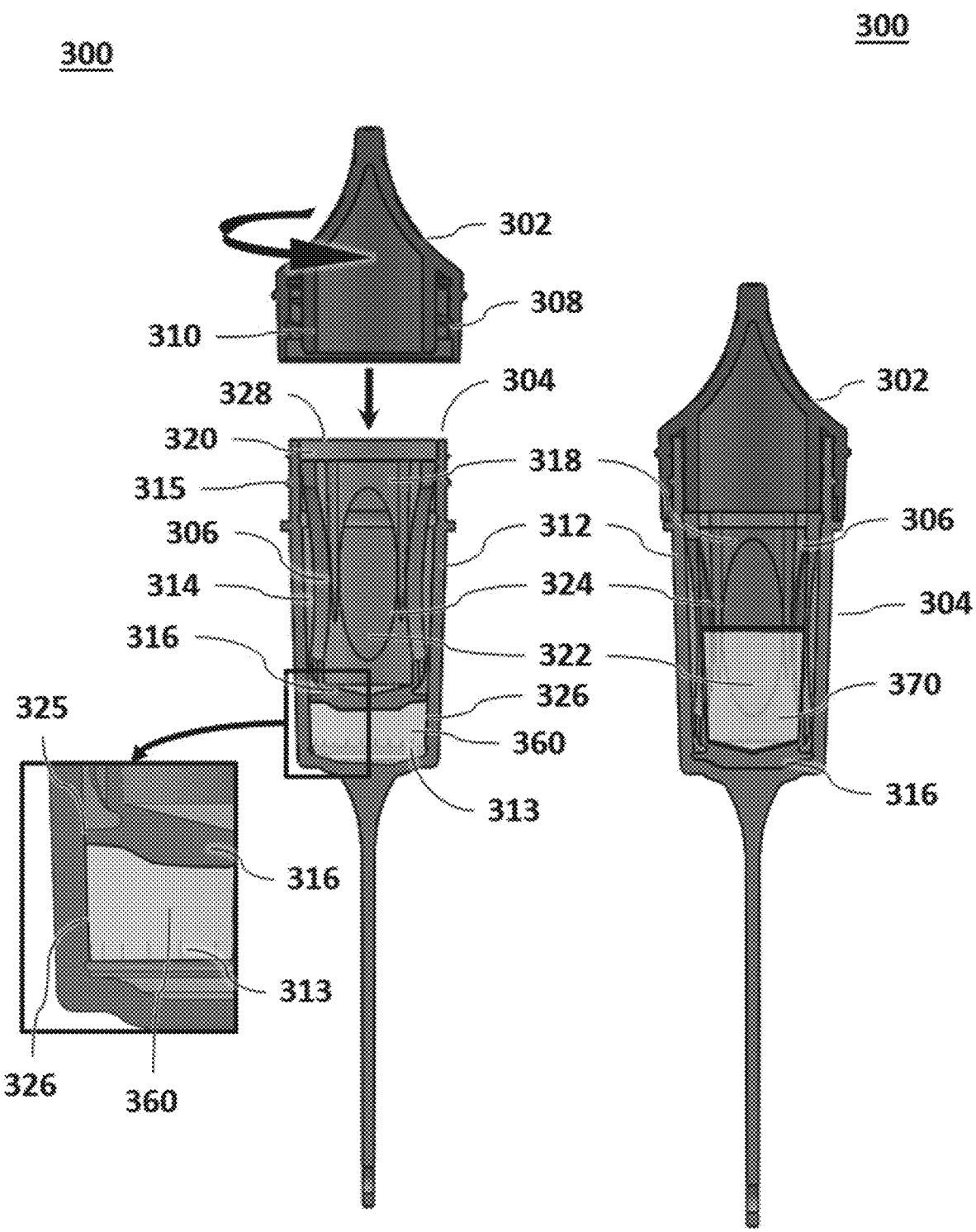
FIG. 3A shows a cross-sectional view of another sample collection device in an open position, according to an embodiment.
FIG. 3B shows a cross-sectional view of the sample collection device of FIG. 3A in a closed position, according to an embodiment.

FIG. 3A shows a cross-sectional view of another sample collection device 300 in an open position. FIG. 3B shows a cross-sectional view of the sample collection device 300 in a closed position. The sample collection device 300 can comprise a lid 302, a vessel 304, and an implement 306.

The lid 302 can comprise a first vessel engagement unit 308 and a second vessel engagement unit 310. The first vessel engagement unit 308, for example, can be threads. The second vessel engagement unit 310, for example, can be a protrusion configured to contact one or more components of the vessel 304 and/or the implement 306.

The vessel 304 can comprise one or more walls 312 that define a cavity 314 with an open end and a closed end. The one or more walls 312 can comprise a first lid engagement unit 315. The first lid engagement unit 315, for example, can comprise threads complementary to the first vessel engagement unit 310. The one or more walls 312 can comprise one or more serrations 313 facing or emanating into the inside of the cavity 314 located at and/or in proximity to the closed end or the bottom of the vessel. The number of serrations and distance between serrations may optionally be varied depending on the size (e.g., length and diameter) of the vessel and/or the size of the serrations. For example, if the vessel is configured to have a larger diameter at the closed end or bottom, more serrations may be included. The number of serrations may be from 1 to 6, 4 to 10, 8 to 16, 14 to 20, 18 to 40, 30 to 60, 40 to 100, 90 to 120, 100 to 150, 125 to 175, 150 to 200, 175 to 300, 200 to 400, or more, depending on the size of serrations. Alternatively, the number of serrations may be outside the above-recited ranges. The serrations 313 can be located at about 10 centimeters (cm), 9 cm, 8 cm, 7 cm, 6 cm, 5 cm, 4 cm, 3 cm, 2 cm, 1 cm, or less, or 10 millimeters (mm), 9 mm, 8 mm, 7 mm, 6 mm, 5 mm, 4 mm, 3 mm, 2 mm, 1 mm, or less, distance from the inner wall of the closed end. Alternatively, the serrations 313 may be located more than 10 cm distance from the inner wall of the closed end. In some cases, the location of the serrations may depend on the size (e.g., length) of the vessel.

The serrations 313 can be micro-serrations. In some instances, the serrations 313 can be protrusions or micro-protrusions. The serrations 313 and/or protrusions can have sharp, jagged, and/or cutting edges. Alternatively or in addition, the serrations 313 can have rounded edges. In some instances, the serrations 313 can be molded or otherwise integrated in the one or more walls 312. Alternatively or in addition, the serrations 313 can be separate structures fastened to be fixed to the one or more walls 312.

The implement 306 can be displaceable, injectable, plungeable, retractable, dejectable, ascendible, descendible, and/or otherwise be movable or actuated relative to the vessel 302. For example, the implement 306 can be a plunger. The implement 306 can be a second vessel, tube or vial. The implement 306 can be a rod, stage, plate, or other actuator. Any description herein of a plunger may apply to any other implement, such as a rod, stage, plate, or other actuator.

The implement 306 can be disposed in the cavity 314. The implement 306 can be insertable in the cavity 314 towards the closed end. The implement 306 can comprise a base plate 316, one or more sidewalls 318, and a second lid engagement unit 320. The one or more sidewalls 318 and the baseplate 316 can define a reservoir 322 for receiving a biological sample (not shown) from a user. In some instances, the baseplate 316 can be part (e.g., an integral part, a monolithic part, etc.) of the one or more sidewalls 318. The baseplate 316 can be located towards the closed end of the cavity 314. The baseplate 316 can be flat, curved, or have any other surface profile. The user may be a subject from whom the sample is collected. The one or more sidewalls 318 can comprise one or more openings 324 through which the reservoir 322 and the cavity 314 are in fluid communication. The second lid engagement unit 320 can engage with the second vessel engagement unit 310 of the lid 302. In some instances, the second lid engagement unit 320 can be part of the one or more sidewalls 318 of the implement 306. During closing of the vessel 304, the second vessel engagement unit 310 (e.g., protrusion) of the lid 302 can apply a force (e.g., via push, press) on the second lid engagement unit 320 (e.g., sidewall perimeter) to actuate the implement 306 and inject the implement 306 towards the closed end of the cavity 314.

The base plate 316 can span the cross-section of the cavity 314 to provide a seal 325 between the base plate 316 and the non-serrated portions of the one or more walls 312 defining the cavity 314. The seal 325 can be a wiper seal. The seal 325 can be a fluid-tight seal. The seal 325 can be a hermetic seal. The seal 325 can be provided via an interference fit between the outer dimension of the base plate 316 and the inner dimension of the one or more walls 316. The base plate 316 and the one or more walls 316 may comprise the same or different materials (e.g., polypropylene and polyethylene, etc.). The seal 325 can be maintained between the non-serrated (or non-protruded) portion of the one or more walls 312 as the implement 306 is injected (or dejected).

Thus, the base plate 316 can partition the cavity 314 to define a reagent chamber 326 that is fluidically isolated from the remainder of the cavity 314. The base plate 316 and the one or more walls 312 at or in proximity to the closed end of the cavity 314 can define the reagent chamber 326. The reagent chamber 326 can be fluidically isolated from the reservoir 322 which is in fluid communication with the rest of the cavity 314. The reagent chamber 326 can comprise a preservation and/or stabilization reagent 360.

When the device 300 is in an open position (as in FIG. 3A), the base plate 316 can be located above the serrated and/or protruded portion of the one or more walls 312 such that the seal 325 is intact and the reagent chamber 326 is fluidically isolated from the reservoir 322.

To alternate the device 300 to the closed position (as in FIG. 3B), the lid 302 can be brought in proximity to the vessel 304. The first vessel engagement unit 308 (e.g., threads) in the lid 302 can engage with the first lid engagement unit 315 (e.g., complementary threads) in the vessel 304 to couple the lid 302 and the vessel 304. For example, the lid 302 can descend onto the vessel 304 in a threading motion. As the lid 302 descends, the second vessel engagement unit 310 (e.g., protrusion) in the lid 302 can engage the second lid engagement unit 320 (e.g., sidewall perimeter) of the implement 306, and translate the descending motion to actuate the implement 306 and inject the implement 306 towards the closed end of the cavity 314 of the vessel 302.

As the implement 306 is injected, the base plate 316 of the implement can continue to provide the seal 325 between the one or more walls 312 of the vessel 302 and the base plate 316 until the base plate 316 engages the one or more serrations 313 on the one or more walls 312 of the vessel 302 and the seal 325 is disrupted. For example, the protrusions and/or serrations may reduce the contact area of the seal 325 to bring the reagent chamber 326 in fluid communication with the remainder of the cavity 314 and, by extension, to the reservoir 322 via the one or more openings 324. As the implement 306 is injected, and the reagent chamber 326 decreases in volume, the reagent 360 may flow around the disrupted seal 325 into the cavity 314 and into the reservoir 322 to form a mixture 370 of the biological sample (not shown) and the reagent 360. The reagent 360 may preserve and/or stabilize the biological sample in the mixture 370.

In application, the device 300 is provided to the user in an open position (as in FIG. 3A). The reagent 360 is pre-loaded in the reagent chamber 326 and the implement 306 is disposed in the vessel 304 such that the base plate 316 is interfacing a non-serrated portion of the one or more walls 312 and the seal 325 is intact. The implement 306 is insertable into the vessel 304. The user spits or otherwise deposits the biological sample (not shown) into the reservoir 322 through an opening 328 of the reservoir 322. In some instances, the opening 328 of the reservoir 322 can be the only opening to the vessel 304. The biological sample and the reagent 360 are fluidically isolated.

The user can close the opening 328 of the reservoir 322 with the lid 302, such as by engaging the first vessel engagement unit 308 of the lid 302 and the first lid engagement unit 315 of the vessel 304. Upon descent of the lid 302, the second vessel engagement unit 310 of the lid 302 can engage the second lid engagement unit 320 of the implement 308, and the implement 308 can be injected towards the closed end of the cavity 314. Once injected, the base plate 316 of the implement 306 engages the one or more serrations 313 on the one or more walls 312 of the vessel 304 and the seal 325 is disrupted. The reagent chamber 326 and the remaining cavity 314 space are brought into fluid communication. As the implement decreases the volume of the reagent chamber 326, the reagent 360 escapes the reagent chamber 326 around or through the disrupted seal 325 to enter the remaining cavity 314 space and thereafter enter the reservoir 322 through the one or more openings 324 on the one or more sidewalls 318 of the implement 306.

The biological sample and the reagent 360 form a mixture 370 of the biological sample and the reagent 360. The reagent 360 can preserve and/or stabilize the biological sample in the mixture 370. The mixture 370 may be stored in the reservoir 322 and/or the cavity 314.

The device 300 can be configured such that the implement 306 is fully injected (as in FIG. 3B) when the lid 302 is securely fastened to the vessel 304. When the implement 306 is fully injected, the base plate 316 may contact the closed end of the cavity 314 such that there is substantially no volume in the reagent chamber 326 and as a result all of the reagent 360 comes in contact with the biological sample to form the mixture 370. Alternatively, when the lid 302 is securely fastened to the vessel 304, the implement 306 may be partially injected, and the base plate 316 may not necessarily contact the closed end of the cavity 314.

In some instances, once injected, the implement 306 can lock in the injected position such that it cannot be dejected and the mixture 370 stays in the reservoir 322 and/or cavity 314 space above the base plate 316. In other instances, after injection, the implement 306 can be un-injected (or dejected), such as when the lid 302 is removed and the mixture 370 may travel between the reservoir 322, cavity 314, and/or the reagent chamber 326. In some instances, the implement 306 may not be removed from the vessel 304 by the user. For example, a cross-section of a pre-inserted part of the implement 306 may be larger than a cross-section of the open end of the cavity 314.

In some instances, the seal 325 may re-seal after disruption when the base plate 316 returns to interfacing a non-serrated portion of the one or more walls 312 of the vessel 304. Alternatively, the seal 325 may remain disrupted even after the base plate 316 returns to interfacing a non-serrated portion of the one or more walls 312 of the vessel 304.

The user may transport the closed device 300, such as via shipping, to a remote location such as an outside lab for further processing and/or analysis. The device 300 may be shipped in a container with or without insulation. For example, the container can be an envelope, packaging, and/or a box. The device 300 may withstand routine forces received in shipping environments.

In some instances, in the open position (as in FIG. 3A) the reagent chamber 326 may be fully pre-loaded with the reagent 360 to fill the reagent chamber 326. Alternatively, the reagent chamber 326 may be partially pre-loaded with the reagent 360.

In some instances, the one or more walls 312 of the vessel 304 or other components of the vessel 304 and/or the implement 306 may comprise one or more markings corresponding to fluid volume for reference to users (e.g., sample origin, lab technician, etc.) of the device 300. For example, one or more markings may correspond to a volume of the reagent 360 in the reagent compartment 326. One or more markings may correspond to a volume of the biological sample in the reservoir 322. One or more marking may correspond to a volume of the mixture 370 in the reservoir 322 and/or the cavity 314. In some instances, at least a part of the one or more walls 312 of the vessel may be at least partially transparent and/or translucent, or clear, to permit visual recognition of the one or more markings. In some instances, at least a part of the other components of the vessel 304 and/or the implement 306 can be at least partially transparent and/or translucent, or clear, to permit visual recognition of the one or more markings.

While FIGS. 3A and 3B illustrate a device with the reservoir 322 and the reagent chamber 326 as generally vertically neighboring compartments, other configurations are available. For example, the reservoir 322 and the reagent chamber 326 can be horizontally neighboring compartments, diagonally neighboring compartments, or placed relative to the other in any other orientation relative to the cavity 314.

In some instances, the user can deposit the biological sample into the reservoir 322 on a carrier. For example, the carrier can be an absorbent member, such as a swab, cotton, pad, sponge, foam, or other material or device capable of carrying the biological sample by absorbing. When the reagent 360 is directed to the reservoir 322 by actuation of the implement 306, the absorbent member may absorb the reagent 360, thereby contacting the biological sample therein with the reagent 360 to preserve and/or stabilize the biological sample. The carrier can be other materials or device capable of carrying the biological sample in a location that is in fluid communication with the reservoir 322 such as to allow the reagent 360 to contact the biological sample on the carrier.

In an example, the user uses the device 300 to collect the biological sample (e.g., saliva or cheek swab) from a subject. The user can be the subject. Alternatively, the user can be one or more other individuals (e.g., supervisor, guardian, lab technician, worker, etc.) that collect the biological sample from the subject. The biological sample is deposited into the reservoir 322 through the opening 328. Next, the user closes the vessel 304 with the lid 302, such as by engaging (e.g., threading) the lid 302 with the vessel 304. Upon engagement, the lid 302 actuates the implement 306, such as by pushing the implement 306 inwards the vessel 304. Actuation of the implement 306 brings the reagent chamber 326 in fluid communication with the reservoir 322. The reagent 360 is directed into the reservoir 322 and forms a mixture 370 with the biological sample. The closed device 300 is then transported (e.g., via mail), such as to a remote lab for further processing and/or analysis. The biological sample is preserved and/or stabilized during such transportation with aid of the reagent 360.

Any description herein of a biological sample with reference to the device 300 can apply to a liquid sample. Any description herein of a reagent (e.g., reagent 360) with reference to the device 300 can apply to a liquid solution. For example, the device 300 may be pre-loaded with a liquid solution and facilitate collection of a liquid sample.

Figure 4:
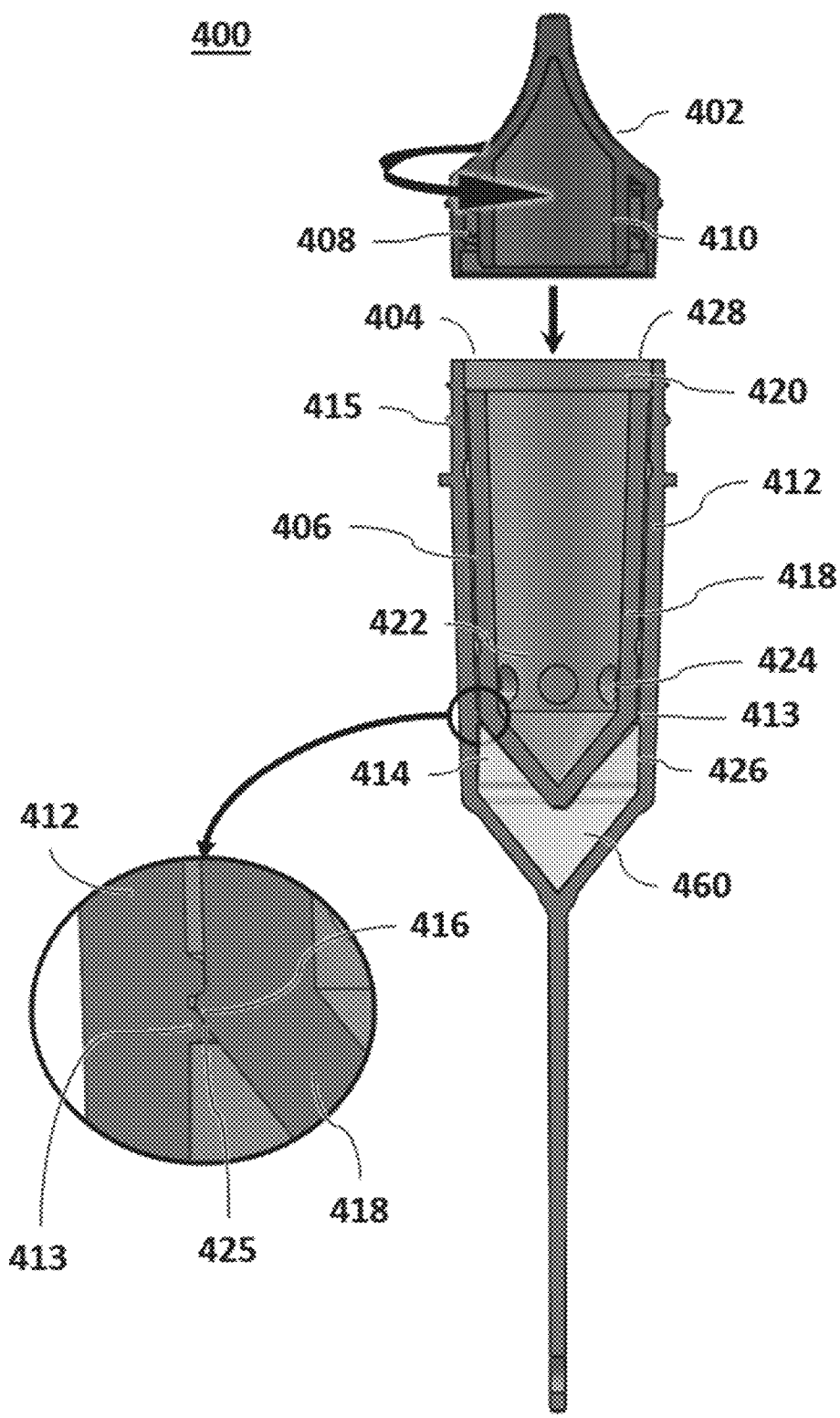
FIG. 4 shows a cross-sectional view of another sample collection device in an open position, according to an embodiment.

FIG. 4 shows a cross-sectional view of another sample collection device 400 in an open position. The sample collection device 400 can comprise a lid 402, a vessel 404, and an implement 406.

The lid 402 can comprise a first vessel engagement unit 408 and a second vessel engagement unit 410. The first vessel engagement unit 408, for example, can be threads. The second vessel engagement unit 410, for example, can be a protrusion configured to contact one or more components of the vessel 404 and/or the implement 406.

The vessel 404 can comprise one or more walls 412 that define a cavity 414 with an open end and a closed end. The one or more walls 412 can comprise a first lid engagement unit 415. The first lid engagement unit 415, for example, can be threads complementary to the first vessel engagement unit 410. The one or more walls 412 can comprise one or more protrusions 413 facing the inside of the cavity 414 located in proximity to the closed end. For example, the protrusions 413 can be located at most 10 centimeters (cm), 9 cm, 8 cm, 7 cm, 6 cm, 5 cm, 4 cm, 3 cm, 2 cm, 1 cm, or less distance from the inner wall of the closed end. The protrusions 413 can be micro-protrusions. The protrusions 413 can be annular features. Alternatively or in addition, the protrusions 413 can extend with substantially even height around a cross-section perimeter (not necessarily circular or curved) of an inner surface of the vessel 404. In FIG. 4, two sets of annular protrusions are illustrated. In some instances, the protrusions 413 can be molded or otherwise integrated in the one or more walls 412. Alternatively or in addition, the protrusions 413 can be separate structures fastened to be fixed to the one or more walls 412.

The implement 406 can be displaceable, injectable, plungeable, retractable, dejectable, ascendible, descendible, and/or otherwise be movable or actuated relative to the vessel 404. For example, the implement 406 can be a plunger. The implement 406 can be a second vessel, tube or vial. The implement 406 can be a rod, stage, plate, or other actuator. Any description herein of a plunger may apply to any other implement, such as a rod, stage, plate, or other actuator.

The implement 406 can be disposed in the cavity 414. The implement 406 can be insertable in the cavity 414 towards the closed end. The implement 406 can comprise a protrusion 416, one or more sidewalls 418, and a second lid engagement unit 420. The one or more sidewalls 418 can define a reservoir 422 therein for receiving a biological sample (not shown) from a user. The user may be a subject from whom the sample is collected. The one or more sidewalls 418 can comprise one or more openings 424 through which the reservoir 422 and the cavity 414 are in fluid communication. The second lid engagement unit 420 can engage with the second vessel engagement unit 410 of the lid 402. In some instances, the second lid engagement unit 420 can be part of the one or more sidewalls 418 of the implement. During closing of the vessel 404, the second vessel engagement unit 410 (e.g., protrusion) of the lid 402 can apply a force (e.g., via push, press) on the second lid engagement unit 420 (e.g., sidewall perimeter) to actuate the implement 406 and inject the implement 406 towards the closed end of the cavity 414.

The one or more sidewalls 418 of the implement 406 can comprise a protrusion 416 towards the end of the implement 406 that is closer to the closed end of the cavity 414. The protrusion 416 can be an annular feature. Alternatively or in addition, the protrusion 416 can extend with substantially even height around a cross-section perimeter (not necessarily circular or curved) of an outer surface of the implement 406. In FIG. 4, an annular protrusion is illustrated. In some instances, the protrusion 416 can be molded into or otherwise integrated as part of the one or more sidewalls 418. In some instances, the protrusion 416 can be separate structures fastened and fixed on the one or more sidewalls 418.

In an open position (as in FIG. 4) the protrusion 416 on the one or more sidewalls 418 of the implement 406 can engage with the one or more protrusions 413 on the one or more walls 412 of the vessel 404 to provide a seal 425 between the respective walls of the implement 406 and the vessel 404. The seal 425 can be a fluid-tight seal. The seal 425 can be a hermetic seal. The seal 425 can be an interference seal. For example, the cross-section dimension (e.g., outer diameter) of the implement 406 with the protrusion 416 can be greater than the cross-section dimension (e.g., inner diameter) of the cavity 414 with the one or more protrusions 413. The cross-section dimension (e.g., outer diameter) of the implement 406 with the protrusion 416 can be less than the cross-section dimension (e.g., inner diameter) of the cavity 414 without the one or more protrusions 413 such as to allow for fluid movement between the two cross-sections when the respective protrusions are unengaged. In some instances, the one or more walls 412 of the vessel may comprise at least two protrusions spaced accordingly to sandwich the protrusion 416, such that the implement 406 is fixed in place prior to application of force while providing the seal 425.

A reagent chamber 426 can be defined between the closed end of the cavity 414 and the seal 425. The reagent chamber 426 can comprise a preservation and/or stabilization reagent 460 for preserving and/or stabilizing the biological sample. The reagent chamber 426 can be fluidically isolated from the remainder of the cavity 414. The reagent chamber 426 can be fluidically isolated from the reservoir 422 which is in fluid communication with the rest of the cavity 414.

When the device 400 is in an open position (as in FIG. 4), the protrusion 416 can be engaged with the one or more protrusions 413 such that the seal 425 is intact and the reagent chamber 426 is fluidically isolated from the reservoir 422.

To alternate the device 400 to the closed position (not shown), the lid 402 can be brought in proximity to the vessel 404. The first vessel engagement unit 408 (e.g., threads) in the lid 402 can engage with the first lid engagement unit 415 (e.g., complementary threads) in the vessel 404 to couple the lid 402 and the vessel 404. For example, the lid 402 can descend onto the vessel 404 in a threading motion. As the lid 402 descends, the second vessel engagement unit 410 (e.g., protrusion) in the lid 402 can engage the second lid engagement unit 420 (e.g., sidewall perimeter) of the implement 406, and translate the descending motion to actuate the implement 406 and inject the implement 406 towards the closed end of the cavity 414 of the vessel 402.

As the implement 406 is injected, the protrusion 416 can move past the interference of the one or more protrusions 413, thereby disrupting the seal 425. This can bring the reagent chamber 426 in fluid communication with the remainder of the cavity 414 and, by extension, to the reservoir 422 via the one or more openings 424. As the implement 406 is injected, and the reagent chamber 426 decreases in volume, the reagent 460 may flow around the one or more sidewalls 418 of the implement 406 into the cavity 414 and into the reservoir 422 via the one or more openings 424 to form a mixture of the biological sample (not shown) and the reagent 460. The reagent 460 may preserve and/or stabilize the biological sample in the mixture.

In application, the device 400 is provided to the user in an open position (as in FIG. 4). The reagent 460 is pre-loaded in the reagent chamber 426 and the implement 406 is disposed in the vessel 404 such that the protrusion 416 is engaged with the one or more protrusions 413 and the seal 425 is intact. The implement 406 is insertable into the vessel 404. The user spits or otherwise deposits the biological sample (not shown) into the reservoir 422 through an opening 428 of the reservoir 422. In some instances, the opening 428 of the reservoir 422 can be the only opening to the vessel 404. The biological sample and the reagent 460 are fluidically isolated.

The user can close the opening 428 of the reservoir 422 with the lid 402, such as by engaging the first vessel engagement unit 408 of the lid 402 and the first lid engagement unit 415 of the vessel 404. Upon descent of the lid 402 relative to the vessel 404, the second vessel engagement unit 410 of the lid 402 can engage the second lid engagement unit 420 of the implement 406, and the implement 406 can be injected towards the closed end of the cavity 414. Once injected, the protrusion 416 moves past the one or more protrusions 413 thus becoming disengaged and the seal 425 is disrupted. The reagent chamber 426 and the remaining cavity 414 space are brought into fluid communication. As the implement 406 decreases the volume of the reagent chamber 426, the reagent 460 escapes the reagent chamber 426 around the one or more sidewalls 418 of the implement 406 to enter the remaining cavity 414 space and thereafter enter the reservoir 422 through the one or more openings 424 on the one or more sidewalls 418 of the implement 406. The biological sample and the reagent 460 form a mixture of the biological sample and the reagent 460. The reagent 460 can preserve and/or stabilize the biological sample in the mixture. The mixture may be stored in the reservoir 422 and/or the cavity 414.

The device 400 can be configured such that the implement 406 is fully injected when the lid 402 is securely fastened to the vessel 404. When the implement 406 is fully injected, a tip of the implement 406 may contact the closed end of the cavity 414 such that there is substantially no volume in the reagent chamber 426 and as a result all of the reagent 460 comes in contact with the biological sample to form the mixture. In some instances, the tip of the implement 406 and the closed end of the cavity 414 can be complementary shapes or figures (e.g., conical pairs as shown in FIG. 4). Alternatively, when the lid 402 is securely fastened to the vessel 404, the implement 406 may be partially injected, and the tip of the implement 406 may not necessarily contact the closed end of the cavity 414.

In some instances, once injected, the implement 406 can lock in the injected position such that it cannot be dejected and the mixture stays in the reservoir 422 and/or cavity 414 space above the protrusion 416. In other instances, after injection, the implement 406 can be un-injected, such as when the lid 402 is removed and the mixture may travel between the reservoir 422, cavity 414, and/or the reagent chamber 426. In some instances, the implement 406 may not be removed from the vessel 404 by the user. For example, a cross-section of a pre-inserted part of the implement 406 may be larger than a cross-section of the open end of the cavity 414.

Alternatively or in addition, the implement 406 may be removable from the vessel, such as by a lay user or lab technician.

In some instances, the seal 425 may re-seal after disruption when the respective protrusions re-engage. Alternatively, the seal 425 may remain disrupted after the first disruption by the user. For example, the first disruption may or may not permanently damage (e.g., break off) the one or more protrusions 313 or the protrusion 316.

The user may transport the closed device 400, such as via shipping, to a remote location such as an outside lab for further processing and/or analysis. The device 400 may be shipped in a container with or without insulation. For example, the container can be an envelope, packaging, and/or a box. The device 400 may withstand routine forces received in shipping environments.

In some instances, in the open position (as in FIG. 4) the reagent chamber 426 may be fully pre-loaded with the reagent 460 to fill the reagent chamber 426. Alternatively, the reagent chamber 426 may be partially pre-loaded with the reagent 460.

In some instances, the one or more walls 412 of the vessel 404 or other components of the vessel 404 and/or the implement 406 may comprise one or more markings corresponding to fluid volume for reference to users (e.g., sample origin, lab technician, etc.) of the device 400. For example, one or more markings may correspond to a volume of the reagent 460 in the reagent compartment 426. One or more markings may correspond to a volume of the biological sample in the reservoir 422. One or more marking may correspond to a volume of the mixture in the reservoir 422 and/or the cavity 414. In some instances, at least a part of the one or more walls 412 of the vessel may be at least partially transparent and/or translucent, or clear, to permit visual recognition of the one or more markings. In some instances, at least a part of the other components of the vessel 404 and/or the implement 406 can be at least partially transparent and/or translucent, or clear, to permit visual recognition of the one or more markings.

While FIG. 4 illustrates a device with the reservoir 422 and the reagent chamber 426 as generally vertically neighboring compartments, other configurations are available. For example, the reservoir 422 and the reagent chamber 426 can be horizontally neighboring compartments, diagonally neighboring compartments, or placed relative to the other in any other orientation relative to the cavity 414.

In some instances, the user can deposit the biological sample into the reservoir 422 on a carrier. For example, the carrier can be an absorbent member, such as a swab, cotton, pad, sponge, foam, or other material or device capable of carrying the biological sample by absorbing. When the reagent 460 is directed to the reservoir 422 by actuation of the implement 306, the absorbent member may absorb the reagent 460, thereby contacting the biological sample therein with the reagent 460 to preserve and/or stabilize the biological sample. The carrier can be other materials or device capable of carrying the biological sample in a location that is in fluid communication with the reservoir 422 such as to allow the reagent 460 to contact the biological sample on the carrier.

In an example, the user uses the device 400 to collect the biological sample (e.g., saliva or cheek swab) from a subject. The user can be the subject. Alternatively, the user can be one or more other individuals (e.g., supervisor, guardian, lab technician, worker, etc.) that collect the biological sample from the subject. The biological sample is deposited into the reservoir 422 through the opening 428. Next, the user closes the vessel 404 with the lid 402, such as by engaging (e.g., threading) the lid 402 with the vessel 404. Upon engagement, the lid 402 actuates the implement 406, such as by pushing the implement 406 inwards the vessel 404. Actuation of the implement 406 brings the reagent chamber 426 in fluid communication with the reservoir 422. The reagent 460 is directed into the reservoir 322 and forms a mixture with the biological sample. The closed device 400 is then transported (e.g., via mail), such as to a remote lab for further processing and/or analysis. The biological sample is preserved and/or stabilized during such transportation with aid of the reagent 460.

Any description herein of a biological sample with reference to the device 400 can apply to a liquid sample. Any description herein of a reagent (e.g., reagent 460) with reference to the device 400 can apply to a liquid solution. For example, the device 400 may be pre-loaded with a liquid solution and facilitate collection of a liquid sample.

Figure 5A:
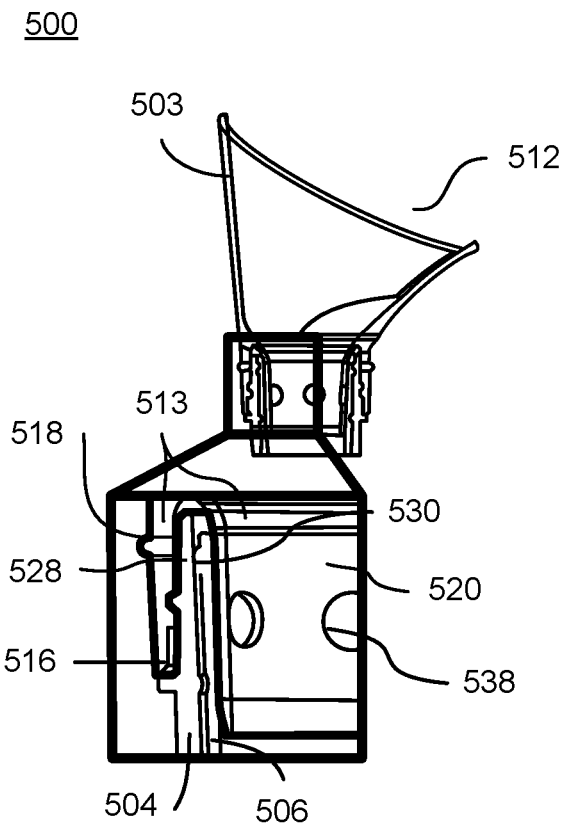
FIG. 5A shows a cross-sectional view of another sample collection device in a funneled position, according to an embodiment.
Figure 5C:
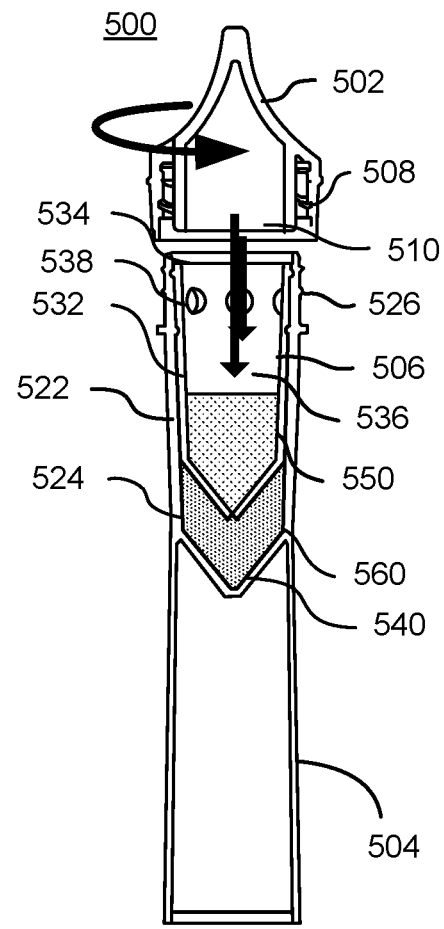
FIG. 5C shows a cross-sectional view of the sample collection device of FIG. 5A in an open position, according to an embodiment.
Figure 5B:
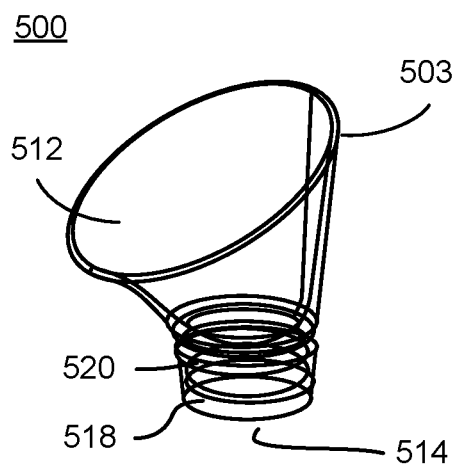
FIG. 5B shows a perspective view of a funnel of the sample collection device of FIG. 5A, according to an embodiment.
Figure 5D:
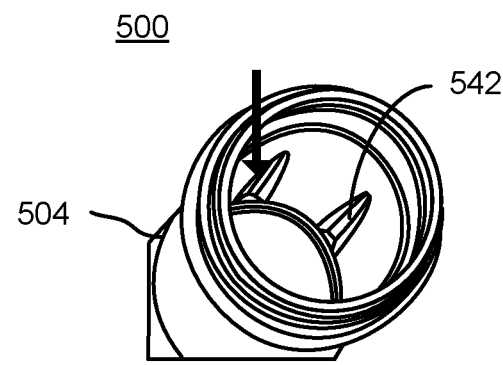
FIG. 5D shows a perspective view of a vessel of the sample collection device of FIG. 5A, according to an embodiment.

FIGS. 5A-5D show another sample collection device 500. The sample collection device 500 can comprise a lid 502, a funnel 503, a vessel 504, and an implement 506. FIG. 5A shows a cross-sectional view of the sample collection device 500 with the funnel 503. FIG. 5B shows a perspective view of the funnel 503. FIG. 5C shows a cross-sectional view of the sample collection device 500 without the funnel 503. FIG. 5D shows a perspective view the vessel 504. The device 500 may comprise a funneled position (as in FIG. 5A), an open position (as in FIG. 5C), and a closed position (not shown).

The lid 502 can comprise a first vessel engagement unit 508 and a second vessel engagement unit 510. The first vessel engagement unit 508, for example, can comprise threads. The second vessel engagement unit 510, for example, can be a protrusion configured to contact one or more components of the vessel 504 and/or the implement 506.

The funnel 503 can comprise a first opening 512 and a second opening 514, and a fluid flow path therethrough. The funnel 503 may receive a biological sample 550 through the first opening 512 and direct the biological sample 550 to exit the funnel 503 through the second opening 514. In some instances, the first opening 512 may have a larger cross-section area than a cross-section area of the second opening 514.

The funnel 503 can comprise a third vessel engagement unit 516 at or near the second opening 514. The third vessel engagement unit 516, for example, can be a pinching structure configured to pinch a wall of the vessel 504 and/or a wall of the implement 506. The pinching structure may be configured to pinch together a wall of the vessel 504 and the wall of the implement 506, for example by applying a force on an inner wall of the implement 506 outwards towards an inner wall of the vessel 504 and/or by applying a force on an outer wall of the vessel 504 inwards towards an outer wall of the implement 506. The pinching structure can be a clip-like structure with two structures biased to pinch. In some instances, the pinching structure can comprise an outer wall 518 and an inner wall 520 defining a cavity therebetween. The outer wall 518 and the inner wall 520 can be configured to pinch one or more objects (e.g., wall of the vessel 504, wall of the implement 506, etc.) disposed in the cavity. In some instances, the pinching structure may comprise threads on the outer wall 518 and/or the inner wall 520 to further engage with the vessel 504.

The vessel 504 can comprise one or more walls 522 that define a cavity 524 with an open end and a closed end. The one or more walls 522 can comprise a first lid engagement unit 526 at or near the open end. The first lid engagement unit 526, for example, can be threads complementary to the first vessel engagement unit 508. The first lid engagement unit 526, for example, can be threads complementary to threads on the third vessel engagement unit 516. The first lid engagement unit 526 may be configured to engage with both the first vessel engagement unit 508 on the lid 502 and the third vessel engagement unit 516 on the funnel 503.

The one or more walls 522 of the vessel 504 can comprise one or more depressions 528 or dents facing the inside of the cavity 524. The depressions 528 or dents can be micro-depressions or micro-dents. The depressions 528 can be annular features. Alternatively or in addition, the depressions 528 can extend with substantially even depth around a cross-section perimeter (not necessarily circular or curved) of an inner surface of the vessel 504. In some instances, the depressions 528 can be molded (or carved out) or otherwise integrated in the one or more walls 522.

The one or more walls 522 of the vessel 504 can comprise one or more vents 542 facing the inside of the cavity 524. The vents 542 may be a depression or dent defining a substantially vertical path from near the closed end of the cavity 524 to near the open end of the cavity 524.

The implement 506 can be displaceable, injectable, plungeable, retractable, dejectable, ascendible, descendible, and/or otherwise be movable or actuated relative to the vessel 504. For example, the implement 506 can be a plunger. The implement 506 can be a second vessel, tube or vial. The implement 506 can be a rod, stage, plate, or other actuator. Any description herein of a plunger may apply to any other implement, such as a rod, stage, plate, or other actuator.

The implement 506 can be disposed in the cavity 524. The implement 506 can be insertable in the cavity 524 towards the closed end. The implement 506 can comprise one or more sidewalls 532 and a second lid engagement unit 534. The one or more sidewalls 532 can define a reservoir 536 therein for receiving the biological sample 550 from a user. The user may be a subject from whom the sample is collected. The one or more sidewalls 532 can comprise one or more openings 538 through which the reservoir 536 and the cavity 524 are in fluid communication. The second lid engagement unit 534 can engage with the second vessel engagement unit 510 of the lid 502. In some instances, the second lid engagement unit 534 can be part of the one or more sidewalls 532 of the implement. During closing of the vessel 504, the second vessel engagement unit 510 (e.g., protrusion) of the lid 502 can apply a force (e.g., via push, press) on the second lid engagement unit 534 (e.g., sidewall perimeter) to actuate the implement 506 and inject the implement 506 towards the closed end of the cavity 524.

The one or more sidewalls 532 of the implement 506 can comprise a protrusion 530 facing the one or more walls 522 of the vessel 504. The protrusion 530 can be an annular feature. Alternatively or in addition, the protrusion 530 can extend with substantially even height around a cross-section perimeter (not necessarily circular or curved) of an outer surface of the implement 506. In some instances, the protrusion 530 can be molded into or otherwise integrated as part of the one or more sidewalls 532. In some instances, the protrusion 530 can be a separate structure fastened and fixed on the one or more sidewalls 532.

In the open position (as in FIG. 5C) or the funneled position (as in FIG. 5A), the protrusion 530 on the one or more sidewalls 532 of the implement 506 can engage with the one or more depressions 528 on the one or more walls 522 of the vessel 504 to retain a position of the implement 506 relative to the vessel 504. In some instances, the engagement of the protrusion 530 and the one or more depressions 528 may provide a seal between the respective walls of the implement 506 and the vessel 504. The seal can be a fluid-tight seal. The seal can be a hermetic seal. The seal can be an interference seal. Alternatively, the engagement of the protrusion 530 and the one or more depressions 528 may not provide a seal.

In the funneled position (as in FIG. 5A), the funnel 503 can be fastened to the vessel 504 upon engagement of the third vessel engagement unit 516 with the vessel 504 and/or the implement 506. When engaged, at least a part of the outer wall 518 of the funnel 503 may encompass at least a portion of the outer wall of the vessel 504 and at least a part of the inner wall 520 of the funnel 503 may be disposed within the reservoir 536 such that the inner wall 520 blocks (or covers) the one or more openings 538 in the one or more sidewalls 532 of the implement 506. When engaged, the outer wall 518 and the inner wall 520 of the funnel 503 can pinch the wall of the vessel 504 and the wall of the implement 506 together to provide a seal between the funnel 503 and the implement 506 and between the funnel 503 and the vessel 504. The seal can be a fluid-tight seal. The seal can be a hermetic seal. The seal can be an interference seal. In the funneled position, the reservoir 536 can be fluidically isolated from the cavity 524 via the seal provided by the funnel 503.

A reagent chamber 540 can be defined between the closed end of the cavity 524 and the one or more sidewalls of the implement 506. The reagent chamber 540 can comprise a preservation and/or stabilization reagent 560 for preserving and/or stabilizing the biological sample 550. In the funneled position, the reagent chamber 540 can be fluidically isolated from the reservoir 536 via the inner wall 520 of the funnel 503 blocking the one or more openings 538 in the one or more sidewalls 532 of the implement 506. The reagent chamber 540 can be brought into fluid communication with the reservoir 536 when the device 500 is in the open position (as in FIG. 5C) and/or the closed position (not shown) upon removal of the funnel 503.

When the device 500 is in an open position (as in FIG. 5C), the funnel 503 can be removed from the vessel 504 such as to unblock the one or more openings 538 in the implement 506. The reagent chamber 540 can be in fluid communication with the reservoir 536. In the open position, the implement 506 may float, or at least partially float, on the reagent 560. The reagent 560 and the biological sample 550 may remain isolated, for example, due to the reagent 560 being unable to overcome gravitational forces to climb the one or more sidewalls 522 of the implement 506 and enter the reservoir 536 through the one or more openings 538 and/or, similarly, the biological sample 550 being unable to overcome gravitational forces to climb the one or more sidewalls 522 of the implement 506 and exit the reservoir 536 through the one or more openings 538.

To alternate the device 500 to the closed position (not shown) from the open position, the lid 502 can be brought in proximity to the vessel 504. The first vessel engagement unit 508 (e.g., threads) in the lid 502 can engage with the first lid engagement unit 526 (e.g., complementary threads) in the vessel 504 to couple the lid 502 and the vessel 504. For example, the lid 502 can descend onto the vessel 504 in a threading motion. As the lid 502 descends, the second vessel engagement unit 510 (e.g., protrusion) in the lid 502 can engage the second lid engagement unit 534 (e.g., sidewall perimeter) of the implement 506, and translate the descending motion to actuate the implement 506 and inject the implement 506 towards the closed end of the cavity 524 of the vessel 502.

As the implement 506 is injected, the protrusion 530 can move past the one or more depressions 528. The implement 506 may intrude the volume of the reagent chamber 540 and displace the reagent 560. The reagent 560 may flow around the one or more sidewalls 418 of the implement 406, such as by travelling through the one or more vents 542 in the one or more walls 522 of the vessel 504, and enter the reservoir 536 via the one or more openings 538. The reagent 560 and the biological sample 550 can form a mixture (not shown). The reagent 560 may preserve and/or stabilize the biological sample 550 in the mixture.

In application, the device 500 is provided to the user in the funneled position (as in FIG. 5A). The reagent 560 is pre-loaded in the reagent chamber 540 and the implement 506 is disposed in the vessel 504 such that the protrusion 530 is engaged with the one or more depressions 528. The funnel 503 is engaged to the vessel 504 and the implement 506 such that the walls of the vessel 504 and the implement 506 are pinched together, and the one or more openings 538 are blocked and sealed by the funnel 503. The implement 506 is insertable into the vessel 504. The user spits or otherwise deposits the biological sample 550 into the reservoir 536 through the first opening 512 of the funnel 503. The funnel 503 directs the biological sample 550 out of the funnel 503 through the second opening 514. The second opening 514 of the funnel is in fluid communication with an opening of the reservoir 536. In some instances, the opening of the reservoir 536 can be the only opening to the vessel 504. The biological sample 550 and the reagent 560 are fluidically isolated via the funnel 503.

The user can remove the funnel 503, thereby unpinching the vessel 504 and the implement 506, and unsealing the one or more openings 538. The reagent chamber 540 and the reservoir 550 are in fluid communication, but the reagent 560 and the biological sample 550 remain isolated. The implement 506 can at least partially float in the cavity 524 on the reagent 560.

The user can close the opening of the reservoir 536 with the lid 502, such as by engaging the first vessel engagement unit 508 of the lid 502 and the first lid engagement unit 526 of the vessel 504. Upon descent of the lid 502 relative to the vessel 504, the second vessel engagement unit 510 of the lid 502 can engage the second lid engagement unit 534 of the implement 508, and the implement 506 can be injected towards the closed end of the cavity 524. Once injected, the protrusion 530 moves past the one or more depressions 528 and intrudes the volume of the reagent chamber 540. The reagent 560 is displaced from the reagent chamber 540 by the implement 506. The reagent 560 escapes the reagent chamber 540 around the one or more sidewalls 532 of the implement 506, such as through the one or more vents 542 to enter the reservoir 536 through the one or more openings 538 on the one or more sidewalls 532 of the implement 506. The biological sample 550 and the reagent 560 form a mixture of the biological sample 550 and the reagent 560. The reagent 560 can preserve and/or stabilize the biological sample 550 in the mixture.

The device 500 can be configured such that the implement 506 is fully injected when the lid 502 is securely fastened to the vessel 504. When the implement 506 is fully injected, a tip of the implement 506 may contact the closed end of the cavity 524 such that there is substantially no volume in the reagent chamber 540 and as a result all of the reagent 560 comes in contact with the biological sample 550 to form the mixture. In some instances, the tip of the implement 506 and the closed end of the cavity 524 can be complementary shapes or figures (e.g., conical pairs as shown in FIG. 5C). Alternatively, when the lid 502 is securely fastened to the vessel 504, the implement 506 may be partially injected, and the tip of the implement 506 may not necessarily contact the closed end of the cavity 524.

In some instances, once injected, the implement 506 can lock in the injected position such that it cannot be dejected and the mixture stays in the reservoir 536 and/or cavity 524 space between the implement 506 and the vessel 504. In other instances, after injection, the implement 506 can be un-injected, such as when the lid 502 is removed and the mixture may travel between the reservoir 536, the cavity 524, and/or the reagent chamber 540. In some instances, the implement 506 may not be removed from the vessel 504 by the user. For example, a cross-section of a pre-inserted part of the implement 506 may be larger than a cross-section of the open end of the cavity 524. Alternatively or in addition, the implement 506 may be removable from the vessel, such as by a lay user or lab technician.

The user may transport the closed device 500, such as via shipping, to a remote location such as an outside lab for further processing and/or analysis. The device 500 may be shipped in a container with or without insulation. For example, the container can be an envelope, packaging, and/or a box. The device 500 may withstand routine forces received in shipping environments.

In some instances, in the funneled position the reagent chamber 540 may be fully pre-loaded with the reagent 560 to fill the reagent chamber 540. Alternatively, the reagent chamber 540 may be partially pre-loaded with the reagent 560.

In some instances, the one or more walls 522 of the vessel 504 or other components of the vessel 504 and/or the implement 506 may comprise one or more markings corresponding to fluid volume for reference to users (e.g., sample origin, lab technician, etc.) of the device 500. For example, one or more markings may correspond to a volume of the reagent 560 in the reagent compartment 540. One or more markings may correspond to a volume of the biological sample 550 in the reservoir 536. One or more marking may correspond to a volume of the mixture in the reservoir 536 and/or the cavity 524. In some instances, at least a part of the one or more walls 522 of the vessel 504 may be at least partially transparent and/or translucent, or clear, to permit visual recognition of the one or more markings. In some instances, at least a part of the other components of the vessel 504 and/or the implement 506 can be at least partially transparent and/or translucent, or clear, to permit visual recognition of the one or more markings.

While FIG. 5 illustrates a device with the reservoir 536 and the reagent chamber 540 as generally vertically neighboring compartments, other configurations are available. For example, the reservoir 536 and the reagent chamber 540 can be horizontally neighboring compartments, diagonally neighboring compartments, or placed relative to the other in any other orientation relative to the cavity 524.

In some instances, the user can deposit the biological sample 550 into the reservoir 536 on a carrier. For example, the carrier can be an absorbent member, such as a swab, cotton, pad, sponge, foam, or other material or device capable of carrying the biological sample by absorbing. When the reagent 560 is directed to the reservoir 536 by actuation of the implement 506, the absorbent member may absorb the reagent 560, thereby contacting the biological sample 550 therein with the reagent 560 to preserve and/or stabilize the biological sample 550. The carrier can be other materials or device capable of carrying the biological sample 550 in a location that is in fluid communication with the reservoir 536 such as to allow the reagent 560 to contact the biological sample 550 on the carrier.

In an example, the user uses the device 500 to collect the biological sample (e.g., saliva or cheek swab) from a subject. The user can be the subject. Alternatively, the user can be one or more other individuals (e.g., supervisor, guardian, lab technician, worker, etc.) that collect the biological sample from the subject. The user receives the device 500 in the funneled position. The biological sample is deposited into the reservoir 536 through the first opening 512 of the funnel 503. Next, the user removes the funnel 503. Next, the user closes the vessel 504 with the lid 502, such as by engaging (e.g., threading) the lid 502 with the vessel 504. Upon engagement, the lid 502 actuates the implement 506, such as by pushing the implement 506 inwards the vessel 504. Actuation of the implement 506 displaces the reagent 560 in the reagent chamber 540. The reagent 560 is directed through the vents 542 and the one or more openings 538 into the reservoir 536. The reagent 560 forms a mixture with the biological sample 550. The closed device 500 is then transported (e.g., via mail), such as to a remote lab for further processing and/or analysis. The biological sample is preserved and/or stabilized during such transportation with aid of the reagent 560.

Any description herein of a biological sample (e.g., biological sample 550) with reference to the device 500 can apply to a liquid sample. Any description herein of a reagent (e.g., reagent 560) with reference to the device 500 can apply to a liquid solution. For example, the device 500 may be pre-loaded with a liquid solution and facilitate collection of a liquid sample.

Figures 6A, 6B:
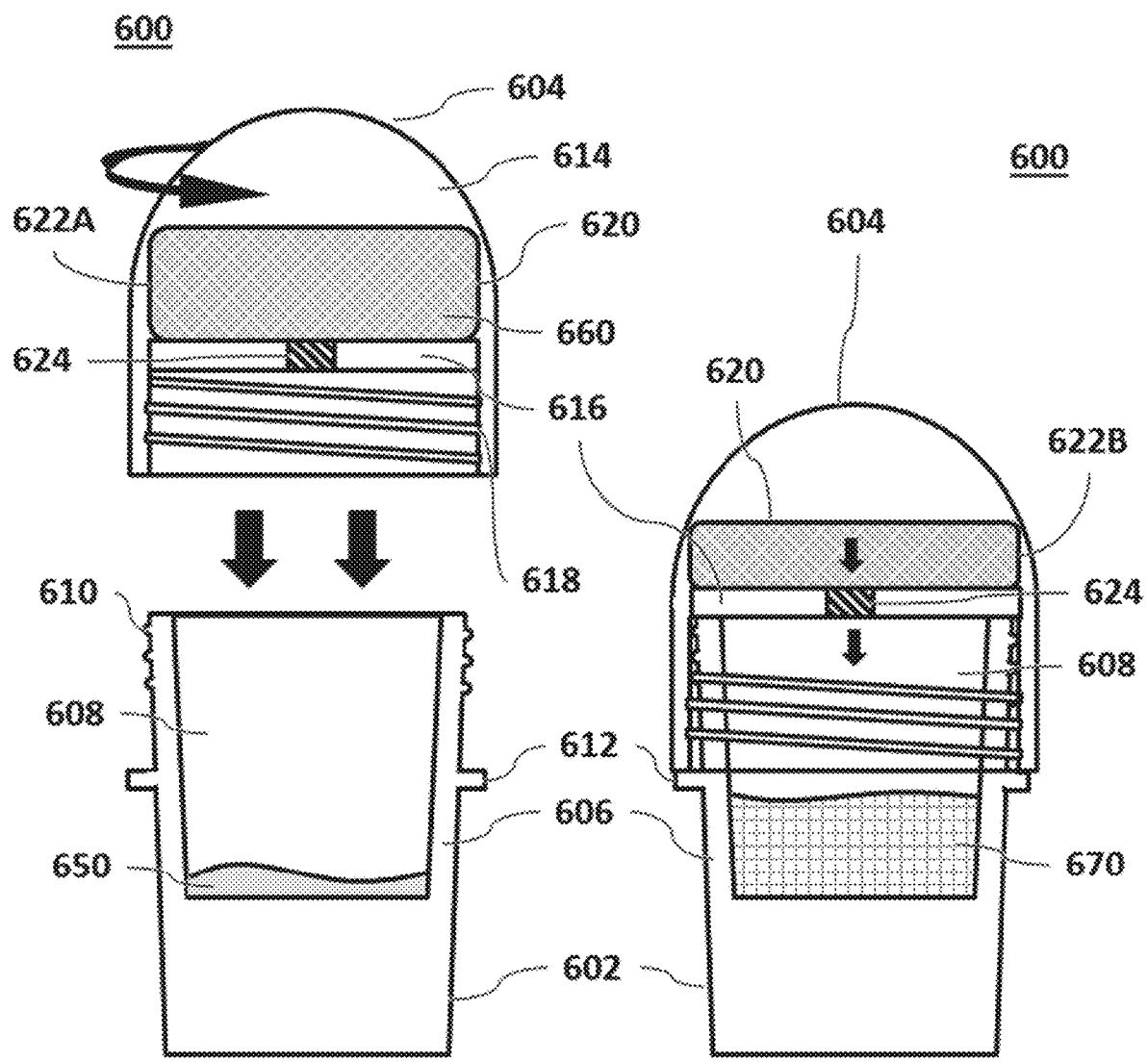
FIG. 6A shows a cross-sectional view of another sample collection device in an open position, according to an embodiment.
FIG. 6B shows a cross-sectional view of the sample collection device of FIG. 6A in a closed position, according to an embodiment.

FIG. 6A shows a cross-sectional view of another sample collection device 600 in an open position. FIG. 6B shows a cross-sectional view of the sample collection device 600 in a closed position. The sample collection device 600 can comprise a vessel 602 and a lid 604.

The vessel 602 can comprise one or more walls 606 that define a reservoir 608 for receiving a biological sample 650 from a user. The user may be a subject from whom the sample is collected. The one or more walls 606 can comprise a lid engagement unit 610, such as threads, to couple with the lid 604. The vessel 602 can comprise rim 612, such as to act as a stopping guide for the lid 604.

The lid 604 can comprise an outer shell 614 and an inner wall 616. The outer shell 614 can comprise a vessel engagement unit 618, such as complementary threads to the lid engagement unit 610.

The inner wall 616 can be mechanically assembled to the outer shell 614. The inner wall 616 and the outer shell 614 can define a reagent chamber 620. The reagent chamber 620 can comprise an absorbent member 622 (A, B). The absorbent member 622 can have absorbed therein a preservation and/or stabilization reagent 660 for preserving and/or stabilizing the biological sample 650. The absorbent member 622 can be compressible (e.g., deformable). For example, the absorbent member 622 can have at least an uncompressed state 622A and a compressed state 622B. The absorbent member 622 can be an absorbent matrix, such as an air matrix or a fiber matrix. The absorbent matrix can be porous. The absorbent member can be formed of a polymeric material. For example, the absorbent member is formed of an absorbent matrix that includes a polymeric material (e.g., poly(vinyl formal) (PVF), polypropylene (PP), (PTFE), polyethylene terephthalate (PET) polyester, polyurethane, ethylene vinyl alcohol, polyvinyl alcohol, polycaprolactone, polylactic acid, starch, etc.). For example, the absorbent member 622 can be a foam or sponge. The absorbent member 622 can be open cell or closed cell foam. In some instances, in the uncompressed state 622A, the absorbent member 622 may retain the reagent 660 absorbed therein without spillage or leakage, such as via capillary action and/or other adhesive/cohesive forces. In some instances, the quantity of reagent 660 loaded into the absorbent member 622 can be controlled for secure containment in the uncompressed state 622A. At least some of the reagent 660 in the absorbent member 622 may exit (e.g., flow out of) the absorbent member 622 upon compression, such as in the compressed state 622B.

When mechanically assembled, the inner wall 616 may move with some degree of freedom relative to the outer shell 614. For example, the inner wall 616 may be capable of moving inwards into the reagent compartment 620 to compress the absorbent member 622. The inner wall 616 can comprise an aperture 624 through which the reagent 660 may leave the reagent chamber 620.

In an open position (as in FIG. 6A), the inner wall 616 may be disposed relative to the outer shell 614 such the absorbent member 622 in the reagent chamber 620 is in an uncompressed state 622A. The reagent chamber 620 can be in fluid communication with spaces external to the reagent chamber 620 via the aperture 624 in the inner wall 616. The reagent 620 absorbed in the absorbent member 622 may remain contained in the absorbent member 622 in the reagent chamber 620.

To alternate to the closed position (as in FIG. 6B), the vessel 602 can be closed with the lid 604 by coupling the vessel engagement unit 618 with the first lid engagement unit 610, such as via a threading motion. Alternatively, other coupling or fastening mechanisms described elsewhere herein may be applied, such as using form-fitting structures, snaps, latches, and/or other fasteners. As the lid 604 descends to cover the vessel 602, the inner wall 616 can engage with the one or more walls 612 of the vessel, such as the top perimeter of the sidewalls. A continued descending motion can push the inner wall 612 into the reagent chamber 620. The absorbent member 622 can compress, such as to compressed state 622B, to accommodate the decreasing volume of the reagent chamber 620. The reagent 660 contained therein the absorbent member 622 may flow out of the absorbent member 622 and into the reservoir 608 which is in fluid communication with the reagent chamber 620 via the aperture 624. The reagent 660 can contact the biological sample 650 in the reservoir 608 to form a mixture 670 with the biological sample 650. The biological sample 650 can thereby be preserved and/or stabilized in the mixture 670.

In application, the user is provided the device 600 in an open position (as in FIG. 6A). The reagent 660 is pre-loaded in the absorbent member 622 in the reagent chamber 620 in the lid 604. The inner wall 616 and the outer shell 614 are mechanically assembled such that the inner wall 614 is not compressing the absorbent member 622. The absorbent member 622 is in the uncompressed state 622A, and the reagent 660 may be contained therein without leakage. The user spits or otherwise deposits the biological sample 650 into the reservoir 608 through an opening of the reservoir 608 in the vessel 602.

The user can close the vessel 602 with the lid 604. As the lid 604 is brought in proximity to the vessel 602, the lid engagement unit 610 (e.g., threads) in the vessel 602 engages the vessel engagement unit 618 (e.g., complementary threads) in the lid 604. The lid 604 descends relative to the vessel 602 until the inner wall 616 engages the top of the one or more walls 505 of the vessel 602. As the lid 604 continues to descend relative to the vessel 602, the inner wall 616 is pushed into the reagent chamber 620 to compress the absorbent member 622. In the compressed state 622B, the absorbent member 622 releases the reagent 660 absorbed therein. The reagent 660 flows into the reservoir 608 via the aperture 624 to form a mixture 670 of the reagent 660 and the biological sample 650. The biological sample 650 can thereby be preserved and/or stabilized in the mixture 670. In some instances, the reagent 660 may flow into the reservoir 608 via gravitational forces.

Thereafter, the lid 604 is fastened to the vessel 602 and the mixture 670 is confined in the reservoir 608 and optionally in the reagent compartment 620 which is in fluid communication with the reservoir 608.

The user may transport the closed device 600, such as via shipping, to a remote location such as an outside lab for further processing and/or analysis. The device 600 may be shipped in a container with or without insulation. For example, the container can be an envelope, packaging, and/or a box. The device 600 may withstand routine forces received in shipping environments.

In some instances, the user can deposit the biological sample 650 into the reservoir 608 on a carrier. For example, the carrier can be an absorbent device, such as a swab, cotton, pad, sponge, foam, or other material or device capable of carrying the biological sample 650 by absorbing. When the reagent 660 flows in the reservoir 608, the absorbent device may absorb the reagent 660, thereby contacting the biological sample 650 therein with the reagent 660 to preserve and/or stabilize the biological sample 650. The carrier can be other materials or devices capable of carrying the biological sample 650 in a location that is in fluid communication with the reservoir 608 such as to allow the reagent 660 to contact the biological sample 650 on the carrier.

In some instances, the inner wall 616 and the outer shell 614 may be mechanically assembled such that the inner wall 616 may move relative to the outer shell 614 with a limited degree of freedom. For example, the inner wall 616 may move relative to the outer shell 614 by at most 10 centimeters (cm), 9 cm, 8 cm, 7 cm, 6 cm, 5 cm, 4 cm, 3 cm, 2 cm, 1 cm, 0.5 cm, or less. Alternatively, the inner wall 616 may move relative to the outer shell 614 by more than 10 cm. In some instances, the inner wall 616 and the outer shell 614 may be mechanically assembled such that the inner wall 616 may move relative to the outer shell 614 in limited directions (e.g., 1 axis, 2 axes, 3 axes, etc.). Alternatively, the inner wall 616 and the sleeve 614 may be mechanically assembled such that the inner wall 616 may move relative to the outer shell 614 in any direction.

In some instances, the inner wall 620 can comprise a plurality of apertures, such as 2, 3, 4, 5, 6, 7, 8, 9, 20, or more apertures. In some instances, the inner wall 620 can comprise a mesh.

In some instances, in the open position (as in FIG. 6A) the uncompressed absorbent member 622A may be fully pre-loaded (e.g., saturated) with the reagent 660. Alternatively, the uncompressed absorbent member 622A may be partially pre-loaded with the reagent 660. For example, the absorbent member 622 can be at least about 1%, 2%, 3%, 4%, 5%, 6%, 7%, 8%, 9%, 10%, 15%, 20%, 25%, 30%, 35%, 40%, 45%, 50%, 60%, 70%, 80%, 90%, 91%, 92%, 93%, 94%, 95%, 96%, 97%, 98%, 99% saturated or higher. Alternatively or in addition, the absorbent member 622 can be at most about 99%, 98%, 97%, 96%, 95%, 94%, 93%, 92%, 91%, 90%, 80%, 70%, 60%, 50%, 45%, 40%, 35%, 30%, 25%, 20%, 15%, 10%, 9%, 8%, 7%, 6%, 5%, 4%, 3%, 2%, 1% saturated or lower. Alternatively or in addition, the absorbent member 622 can be saturated by less than 1% or more than 99%.

In some instances, the one or more walls 606 of the vessel 602 may comprise one or more markings corresponding to fluid volume for reference to users (e.g., sample origin, lab technician, etc.) of the device 600. For example, one or more markings may correspond to a volume of the biological sample 650 in the reservoir 608. One or more marking may correspond to a volume of the mixture 670 in the reservoir 608. In some instances, at least a part of the one or more walls 606 of the vessel 602 may be at least partially transparent and/or translucent, or clear, to permit visual recognition of the one or more markings. In some instances, the outer shell 614 of the lid 604 may comprise one or more markings corresponding to fluid volume for reference to users (e.g., sample origin, lab technician, etc.) of the device 600. For example, one or more markings may correspond to a volume of the reagent 660 or a height of the absorbent member 622 in the reagent compartment 210. In some instances, at least a part of the outer shell 614 of the lid 604 may be at least partially transparent and/or translucent, or clear, to permit visual recognition of the one or more markings.

In some instances, the inner wall 616 may comprise a flexible material. In some instances, the inner wall 616 may be a pierceable, puncturable, tearable, and/or otherwise breakable membrane or barrier that pierces, punctures, tears, and/or breaks when the inner wall 616 engages the side walls of the vessel 602.

In an example, the user uses the device 600 to collect the biological sample 650 (e.g., saliva or cheek swab) from a subject. The user can be the subject. Alternatively, the user can be one or more other individuals (e.g., supervisor, guardian, lab technician, worker, etc.) that collect the biological sample 650 from the subject. The biological sample 650 is deposited into the reservoir 608. Next, the user closes the vessel 602 with the lid 604, such as by engaging (e.g., threading) the lid 604 with the vessel 602. Upon engagement, the inner wall 616 is pushed inwards towards the reagent chamber 620, compressing the absorbent member 622. Upon compression, the reagent 660 that was absorbed in the absorbent member 622 is released from the absorbent member 622 and directed into the reservoir 608 through the aperture 624, and forms a mixture 670 with the biological sample 650. The closed device 600 is then transported (e.g., via mail), such as to a remote lab for further processing and/or analysis. The biological sample 650 is preserved and/or stabilized during such transportation with aid of the reagent 660.

Any description herein of a biological sample (e.g., biological sample 650) with reference to the device 600 can apply to a liquid sample. Any description herein of a reagent (e.g., reagent 660) with reference to the device 600 can apply to a liquid solution. For example, the device 600 may be pre-loaded with a liquid solution and facilitate collection of a liquid sample.

In some instances, one or more portions of a sample collection device may be made of any suitable plastics, such as polypropylene, polystyrene, and/or polycarbonate. For example, an outer component, such as the vessel body and the lid body (e.g., outer shell) may be made of one or more plastics. Alternatively or in addition, one or more portions of the sample collection device may be made of metallic material (e.g., aluminum, etc.), or composite material.

Individual components within the sample collection device (e.g., plunger, protrusions, etc.) may comprise the same or different materials as the body of the device suited for the function of the individual components. The sample collection device may comprise a material resistant (e.g., chemically non-reactive) to the reagent contained therein.

The sample collection device may have varying dimensions. In some instances, the sample collection device may have dimensions smaller than about a standard 500 mL water bottle. In some instances, a closed sample collection device may have a maximum dimension of at most about 20 centimeters (cm), 18 cm, 16 cm, 14 cm, 12 cm, 10 cm, 9 cm, 8 cm, 7 cm, 6 cm, 5 cm, 4 cm, 3 cm, 2 cm, 1 cm or less. Alternatively, a closed sample collection device may have a maximum dimension greater than about 20 cm. In some cases, the closed sample collection device may have a length from about 6 cm to about 15 cm. Alternatively, the closed sample collection device may have a length less than about 6 cm or greater than about 15 cm. In some instances, the device may have a maximum cross-section diameter (e.g., not the length) of about 7 cm, 6 cm, 5 cm, 4 cm, 3 cm, 2 cm, 1 cm or less. Alternatively, the device may have a maximum cross-section diameter of greater than about 7 cm. In some cases, the device may have an outer diameter from about 1 cm to about 2 cm. Alternatively, the device may have an outer diameter less than about 1 cm or greater than about 2 cm. In some instances, a reservoir for receiving a biological sample can have volume dimensions of at most about 200 milliliters (mL), 150 mL, 100 mL, 95 mL, 90 mL, 85 mL, 80 mL, 75 mL, 70 mL, 65 mL, 60 mL, 55 mL, 50 mL, 45 mL, 40 mL, 35 mL, 30 mL, 25 mL, 20 mL, 15 mL, 10 mL, 5 mL, 4 mL, 3 mL, 2 mL, 1 mL or less. Alternatively, the reservoir can have volume dimensions greater than about 200 mL. In some instances, a reagent compartment in a vessel can have volume dimensions of at most about 200 milliliters (mL), 150 mL, 100 mL, 95 mL, 90 mL, 85 mL, 80 mL, 75 mL, 70 mL, 65 mL, 60 mL, 55 mL, 50 mL, 45 mL, 40 mL, 35 mL, 30 mL, 25 mL, 20 mL, 15 mL, 10 mL, 5 mL, 4 mL, 3 mL, 2 mL, 1 mL or less. Alternatively, the reagent compartment in a vessel can have volume dimensions greater than about 200 mL. In some instances, a reagent compartment in a lid can have volume dimensions of at most about 200 milliliters (mL), 150 mL, 100 mL, 95 mL, 90 mL, 85 mL, 80 mL, 75 mL, 70 mL, 65 mL, 60 mL, 55 mL, 50 mL, 45 mL, 40 mL, 35 mL, 30 mL, 25 mL, 20 mL, 15 mL, 10 mL, 5 mL, 4 mL, 3 mL, 2 mL, 1 mL or less. Alternatively, the reagent compartment in a lid can have volume dimensions greater than about 200 mL.

Any embodiment of a sample collection device described herein may comprise from about 0.1 mL to about 5 mL, from about 0.1 mL to about 10 mL, from about 0.1 mL to about 100 mL, from about 5 mL to about 10 mL, from about 5 mL to about 100 mL, from about 10 mL to about 100 mL, or other ranges of the reagent. The sample collection device may comprise less than 0.1 mL of the reagent. The sample collection device may comprise more than about 100 mL of the reagent. In some instances, about an equal volume of each of the biological sample and the reagent can be mixed together, such as within 0.1 mL difference, 1 mL difference, or 10 mL difference of each other.

The sample collection device may be used by a subject from whom the biological sample originates. The sample collection device may be used by an unsophisticated user with or without direct supervision. The sample collection device may be used by a non-subject, such as a technician, guardian, parent, or other individual, to collect the subject's biological sample.

While different embodiments have been shown and described separately, components of different embodiments may be used in various combinations. By way of example, the absorbent member 622 in the reagent chamber 620 in FIGS. 5A and 5B may also be located in the reagent chamber 110 in FIG. 1A, the reagent chamber 326 in FIGS. 3A and 3B, and/or the reagent chamber 426 in FIG. 4.

Kit

In some instances, the sample collection device may be provided as part of a kit. The kit can be a sample collection kit. The kit can be a sample processing kit. The kit can be a sample collection and processing kit. The kit may be provided to a user. In some instances, the user may be a subject from whom the sample is collected. In some instances, the user may be a supervisor, guardian, or assistant of the subject. In some instances, the user may be a lab personnel (e.g., technician, operator, etc.) receiving a sample from the subject.

The kit can comprise one or more sample collection devices as described elsewhere herein. The kit can comprise instructions or a set of instructions for sample collection and/or sample processing. The instructions may be directed to non-sophisticated users, including minors, and/or sophisticated users. The instructions may instruct on how to use a sample collection device, collect a sample using the device, dispose (e.g., ship to a remote location) of the device after use, access results from analysis of the sample, or other instructions. The instructions may provide safety instructions. The instructions can be pictorial. In some instances, the instructions may instruct on how to retrieve a sample from a sample collection device. In some instances, the instructions may instruct on how to process the sample retrieved from a sample collection device.

The kit can comprise one or more containers for shipping the one or more sample collection devices to a remote location, such as a remote lab for further processing and/or analysis. For example, the one or more containers can be boxes, envelopes, and/or other packaging material (e.g., insulating material, self-sealing or other sealing mechanism, postage, etc.). The kit can comprise a return label and/or a prepaid label, such as for use with a mail, shipping, and/or a carrier service. The collected sample may be transported, such as via shipping (e.g., through the mail or a carrier), to a remote lab for further processing and/or analysis.

Sample Processing

Another aspect provides methods for collecting a sample from a subject, receiving the sample and processing the sample. The sample may be collected using any of the sample collection devices provide herein. The sample may be collected from the subject. In an example, the subject may use the sample collection device to collect the sample from the subject directly. As an alternative, another individual (e.g., laboratory technician, nurse, or physician) may use the sample collection device to collect the sample from the subject. The sample collection devices provided herein may retain and/or store the collected sample until the sample is retrieved for further processing and/or analysis.

The collected sample can be transported to a processing center, such as a laboratory or research facility. The processing center can be remote from a point of collection. The collected sample can be transported via shipping (e.g., through the mail or a carrier). During transportation, the sample can be preserved and/or stabilized with aid of the reagents in the sample collection device. The sample may be preserved and/or stabilized on the order of hours, days, weeks, months, and/or years during transportation and/or storage. A sample collection device comprising the collected sample may be received at the processing center. The sample may be retrieved from the sample collection device and processed.

Processing may include nucleic acid amplification, such as via polymerase chain reaction (PCR). The nucleic acid amplification can involve thermal cycling, such as the reiterative cycling of a reaction cocktail between different reaction temperatures. Thermal cycling conditions (e.g., number of thermal cycles, temperatures utilized, cycle time, total run time, etc.) can be controlled to change the different parameters of amplification products. The nucleic acid amplification can be an isothermal amplification. Isothermal amplification can involve amplification at a single and constant temperature or single and constant range of temperature.

Processing may include obtaining sequencing information. Sequencing can include methods and technologies for determining the sequence of nucleotide bases in one or more polynucleotides. The polynucleotides can be, for example, deoxyribonucleic acid (DNA) or ribonucleic acid (RNA), including variants or derivatives thereof (e.g., single stranded DNA).

Sequencing may involve digital PCR. Sequencing can be performed by various systems currently available, such as, without limitation, a sequencing system by Illumina, Pacific Biosciences, Oxford Nanopore, or Life Technologies (Ion Torrent). Sequencing may be next generation sequencing (e.g., Illumina or Pacific Biosciences of California). Sequencing may use a probe array, such as a gene chip (e.g., Affymetrix gene chip). Sequencing may be massively parallel array sequencing (e.g., Illumina) and/or single molecule sequencing (e.g., Oxford Nanopore). Such devices may provide a plurality of raw genetic data corresponding to the genetic information of a subject (e.g., humans), as generated by the device from a sample provided by the subject. Alternatively, or in addition, processing may include proteomic information.

Processing can yield data. The data may be sequencing data. The data may be proteomic data. The processed data may be analyzed to provide an output. The output may be in the form of a report. The report may be an electronic report. The report may be delivered to the subject or another user (e.g., healthcare provider) electronically, such as via electronic mail. The report may be delivered to the subject, over one or more servers and/or networks, such as via a web interface.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A device removably engageable with a funnel and, alternatively, with a lid, the device comprising:
    an outer wall defining a device opening of the device, wherein the outer wall is configured to be engageable with the funnel for the device to receive a DNA sample that is funneled through the device opening and wherein the outer wall is further configured to be engageable with the lid to close the device opening;
    a first chamber defined by the outer wall;
    an inner wall defining an implement; and
    a second chamber included in the implement, wherein the inner wall shares the device opening with the outer wall and further comprises a wall opening for fluid communication between the first chamber and the second chamber, wherein one of the first and second chambers is configured to receive the DNA sample and another of the first and second chambers is configured to store a liquid solution; and
    wherein the inner wall is movable relative to the outer wall so that the implement is movable between a first configuration and a second configuration, wherein the implement in the first configuration closes the wall opening and the implement in the second configuration opens the wall opening for the fluid communication; and wherein the implement is configured to be in the first configuration when the outer wall is engaged with the funnel and configured to be in the second configuration responsive to the lid pushing the implement towards the second configuration, thereby opening the wall opening.

2. The device of claim 1, wherein the device is configured to be engaged with the lid by complementary threading, form-fitting pairs, interference fitting, hooks and loops, latches, screws, staples, clips, clamps, prongs, rings, brads, rubber bands, rivets, grommets, pins, ties, snaps, adhesives, tapes, vacuum, seals, or any combination thereof.

3. The device of claim 1, wherein the first and second chambers are configured to be sealed from an outside environment at the device opening by the lid when the lid is engaged with the device.

4. The device of claim 3, wherein the sealing is fluid-tight.

5. The device of claim 1, wherein the DNA sample is a biological sample selected from saliva, sputum, spit, blood, perspiratory fluid, sweat, pus, a tear, mucosal excretion, vomit, urine, a stool, semen, vaginal fluids, a cell-free sample, a cheek swab, a swab of a different bodily part, a homogenous sample, a heterogeneous sample, a tumor sample, plasma, or a serum sample.

6. The device of claim 1, wherein the liquid solution is a reagent or a DNA stabilization solution.

7. The device of claim 1, wherein the liquid solution comprises reagents that preserve and/or stabilize the DNA sample.

8. The device of claim 1, wherein the first chamber and the second chamber are vertically neighboring compartments, horizontally neighboring compartments, diagonally neighboring compartments, or placed relative to the other in another orientation.

9. The device of claim 1, wherein the device is dimensioned to fit inside a container for shipping the device.

10. A system comprising:
a lid;
a funnel; and
a sample collection device removably engageable with the funnel and, alternatively, with the lid, the sample collection device comprising:
    an outer wall defining a device opening of the device, wherein the outer wall is configured to be engageable with the funnel for the device to receive a DNA sample that is funneled through the device opening and wherein the outer wall is further configured to be engageable with the lid to close the device opening;
    a first chamber defined by the outer wall;
    an inner wall defining an implement; and
    a second chamber included in the implement, wherein the inner wall shares the device opening with the outer wall and further comprises a wall opening for fluid communication between the first chamber and the second chamber, wherein one of the first and second chambers is configured to receive the DNA sample and another of the first and second chambers is configured to store a liquid solution; and
wherein the inner wall is movable relative to the outer wall so that the implement is movable between a first configuration and a second configuration, wherein the implement in the first configuration closes the wall opening and the implement in the second configuration opens the wall opening for the fluid communication; and wherein the implement is configured to be in the first configuration when the outer wall is engaged with the funnel and configured to be in the second configuration responsive to the lid pushing the implement towards the second configuration, thereby opening the wall opening.

* * * * *